United States Patent
Kannicht et al.

(10) Patent No.: US 10,251,940 B2
(45) Date of Patent: Apr. 9, 2019

(54) PREPARATION COMPRISING FACTOR VIII AND VON WILLEBRAND FACTOR PEPTIDES

(71) Applicant: OCTAPHARMA AG, Lachen (CH)

(72) Inventors: Christoph Kannicht, Berlin (DE); Barbara Solecka, Berlin (DE); Guido Kohla, Berlin (DE); Stefan Winge, Arsta (SE)

(73) Assignee: Octapharma AG, Lachen (CH)

( * ) Notice: Subject to any disclaimer, the term of this patent is extended or adjusted under 35 U.S.C. 154(b) by 108 days.

(21) Appl. No.: 15/316,711

(22) PCT Filed: Jun. 8, 2015

(86) PCT No.: PCT/EP2015/062730
§ 371 (c)(1),
(2) Date: Dec. 6, 2016

(87) PCT Pub. No.: WO2015/185758
PCT Pub. Date: Dec. 10, 2015

(65) Prior Publication Data
US 2018/0185455 A1    Jul. 5, 2018

(30) Foreign Application Priority Data
Jun. 6, 2014 (EP) .................................... 14171579

(51) Int. Cl.
| | | |
|---|---|---|
| *A61K 38/00* | (2006.01) | |
| *A61K 38/36* | (2006.01) | |
| *C07K 14/755* | (2006.01) | |
| *A61P 7/04* | (2006.01) | |
| *A61K 38/37* | (2006.01) | |
| *C07K 1/34* | (2006.01) | |
| *C12P 21/02* | (2006.01) | |
| *C12P 21/06* | (2006.01) | |

(52) U.S. Cl.
CPC .............. *A61K 38/36* (2013.01); *A61K 38/37* (2013.01); *A61P 7/04* (2018.01); *C07K 1/34* (2013.01); *C07K 14/755* (2013.01); *C12P 21/02* (2013.01); *C12P 21/06* (2013.01)

(58) Field of Classification Search
None
See application file for complete search history.

(56) References Cited

FOREIGN PATENT DOCUMENTS

| WO | 95/01804 | 1/1995 |
|---|---|---|
| WO | 95/26750 | 10/1995 |
| WO | 2008/151817 | 12/2008 |
| WO | 2013/057167 | 4/2013 |
| WO | 2013/083858 | 6/2013 |
| WO | 2013/160005 | 10/2013 |

OTHER PUBLICATIONS

Marti et al. Identification of Disulfide-Bridged Substructures within Human von Willebrand Factor. Biochemistry 1987, 26, 8099-8109.
Foster et al. A major factor VIII binding domain resides within the amino-terminal 272 amino acid residues of von Willebrand factor. Journal of Biological Chemistry, American Society for Biochemistry and Molecular Biology, vol. 262, No. 18, Jun. 25, 1987, p. 8443-8446.
Fischer et al. Structural analysis of recombinant von Willebrand factor: Identification of hetero- and holm-dimers. FEB Letters, vol. 351, No. 3, Sep. 12, 1994.
Zhou et al. Sequence and structure relationships within von Willebrand factor. Blood, vol. 120, No. 2, Apr. 6, 2012.
Furtan. Von Willebrand factor: molecular size and functional activity. Ann Hematol. Jun. 1996;72(6): 341-8.
Ragni et al. von Willebrand factor: factor VIII protector and friend.Journal of Thrombosis and Haemostatis, 10, 2324-2327.
Viel et al. Inhibitors of Factor VIII in Black Patients with Hemophilia. The New England Journal of Medicine, Apr. 16, 2009, pp. 1618-1627.
Oldenburg et al. Novel Products for haemostasis—current status. Haemophilia (2014), 20 (Suppl. 4), 23-28, Mar. 10, 2014.
Casademunt et al. The first recombinant human coagulation factor VIII of human origin: human cell line and manufacturing charceteristics. European Journal of Haematology 89 (165-176).
Pearson. Effective protein sequence comparison. Methods Enzymol 1996;266:227-58.

*Primary Examiner* — Jeanette M Lieb
(74) *Attorney, Agent, or Firm* — Jacobson Holman PLLC

(57) ABSTRACT

A composition comprising a complex of Factor VIII and one or more Von Willebrand Factor peptides, wherein the Von Willebrand Factor peptides comprise at least the amino acids 764 to 1035 and 1691 to 1905 of SEQ ID No. 1 but not amino acids 2255 to 2645 of SEQ ID No. 1.

19 Claims, 14 Drawing Sheets
Specification includes a Sequence Listing.

PREPARATION COMPRISING FACTOR VIII AND VON WILLEBRAND FACTOR PEPTIDES

The present invention relates to pharmaceutical preparations for treating bleeding disorders.

BACKGROUND OF THE INVENTION

Factor VIII ("FVIII") is a blood plasma glycoprotein of about 280 kDa molecular mass. It is involved in the cascade of coagulation reactions that lead to blood clotting. The most common bleeding disorder is caused by a deficiency of functional Factor VIII, called haemophilia A. It is treated with replacement of Factor VIII, either plasma derived or recombinant. Factor VIII is used for acute and prophylactic treatment of bleedings in haemophilia A patients.

The amino acid sequence of Factor VIII is organized into three structural domains: a triplicated A domain of 330 amino acids, a single B domain of 980 amino acids, and a duplicated C domain of 150 amino acids. The B domain has no homology to other proteins and provides 18 of the 25 potential asparagine(N)-linked glycosylation sites of this protein. The B domain has apparently no function in coagulation. B-domain deleted Factor VIII molecules have unchanged procoagulant activity compared to full-length Factor VIII. Some recombinant Factor VIII (rFVIII) preparations are B-domain deleted.

In plasma, Factor VIII is stabilized by association with Von Willebrand Factor protein ("vWF"), which appears to inhibit clearance of Factor VIII e.g. by proteolysis or receptor-mediated clearance via the LRP-receptor. In circulation, Von Willebrand Factor is present in a 50-fold molar excess relative to Factor VIII under normal physiological conditions.

Von Willebrand Factor is a multimeric adhesive glycoprotein present in the plasma of mammals, which has multiple physiological functions. During primary hemostasis, Von Willebrand Factor acts as a mediator between specific receptors on the platelet surface and components of the extracellular matrix such as collagen. Moreover, Von Willebrand Factor serves as a carrier and stabilizing protein for procoagulant Factor VIII. Von Willebrand Factor is synthesized in endothelial cells and megakaryocytes as a 2813 amino acid precursor molecule. The precursor polypeptide, pre-pro-Von Willebrand Factor, consists of a 22-residue signal peptide, a 741-residue pro-peptide and the 2050-residue polypeptide found in mature plasma Von Willebrand Factor (Fischer et al., FEBS Lett. 351: 345-348, 1994). Upon secretion into plasma, Von Willebrand Factor circulates in the form of various species with different molecular sizes. These Von Willebrand Factor molecules consist of oligo- and multimers of the mature subunit of 2050 amino acid residues. Von Willebrand Factor can be usually found in plasma as multimers ranging in size approximately from 500 to 20.000 kDa (Furlan, Ann Hematol. 1996 June; 72(6):341-8).

The average in vivo half-life of human Factor VIII in the human circulation is approximately 12 hours. Von Willebrand Factor might decrease possible immunoreactions against Factor VIII when in complex with Factor VIII by shielding FVIII from known potential inhibitor antibody sites on the heavy chain (A2 domain) and the light chain (A3/C2 domain) (Ragni, 3 Thromb. Haemost. 10: 2324-2327, 2012) or on other potential antibody inhibitor sites on the Factor VIII molecule.

A further bleeding disorder in humans is Von Willebrand's disease (vWD). Depending on the severity of the bleeding symptoms, vWD can be treated by replacement therapy with concentrates containing Von Willebrand Factor, in general derived from plasma but recombinant Von Willebrand Factor also is under development. Von Willebrand Factor is known to stabilize Factor VIII in vivo and, thus, plays a crucial role to regulate plasma levels of Factor VIII and as a consequence is a central factor to control primary and secondary haemostasis.

Until today, the standard treatment of Haemophilia A and vWD involves frequent intravenous infusions of preparations of Factor VIII and Factor VIII/Von Willebrand Factor concentrates. These replacement therapies are generally effective, however, for example in severe haemophilia A patients undergoing prophylactic treatment Factor VIII has to be administered intravenously (i.v.) about 3 times per week due to the short plasma half life of Factor VIII of about 12 hours. Already by achieving Factor VIII levels above 1% of normal human plasma corresponding to a raise of Factor VIII levels by 0.01 U/ml, severe haemophilia A is turned into moderate haemophilia A. In prophylactic therapy, the dosing regime is designed such that the levels of Factor VIII activity do not fall below levels of 2-3% of the Factor VIII activity of non-haemophiliacs.

The administration of a Factor VIII via intravenous administration (i.v.) is cumbersome, associated with pain and entails the risk of an infection especially as this is mostly done in home treatment by the patients themselves or by the parents of children being diagnosed for haemophilia A. In addition, frequent intravenous injections inevitably result in scar formation, interfering with future infusions. Still, i.v. treatment might be needed in emergency situation or surgery, i.e. when a high Factor VIII-level is needed immediately.

Subcutaneous administration (s.c.) has been proposed for Factor VIII, e.g. in WO 95/01804 A1 and WO 95/026750 A1. However, very high doses of Factor VIII had to be administered to achieve an acceptable bioavailability.

Another approach to improve the bioavailability upon non-intravenous administration has been to use albumin-fused Factor VIII (WO 2011/020866 A2).

WO 2013/057167 A1 proposes to administer Factor VIII in combination with sulphated glycosaminoglycans via non-intravenous administration, optionally together with Von Willebrand Factor.

WO 2008/151817 A1 describes the general use of uncleaved Von Willebrand Factor multimers for stabilisation of Factor VIII, plasma derived or recombinant (full-length and deletion mutants) intended for extravascular treatment.

WO 2013/160005 A1 describes the general use of recombinant Von Willebrand Factor or recombinant Von Willebrand Factor-fragments to improve bioavailability after s.c. treatment for very specific Factor VIII molecules, wherein the said Factor VIII molecules comprise a truncated B domain at a size of 100-400 amino acids. According to WO 2013/160005 A1 Factor VIII molecules with truncated B domains between 100 and 400 amino acids have a higher Factor VIII bioavailability compared to Factor VIII having the entire B domain or B domain truncated Factor VIII molecules having no or only a few amino acids.

There is still a need for Factor VIII preparations showing improved bioavailability, stability and/or lower risk for antibody generation thereby avoiding drawbacks of prior art.

It is the object of the present invention to provide alternative Factor VIII preparations. Preferably, these preparations should show improved stability, improved bioavailability and/or reduced risk for immunological reactions.

In one embodiment, this object is achieved by a composition comprising a complex of Factor VIII and one or more Von Willebrand Factor peptides, wherein the Von Willebrand Factor peptides comprise at least the amino acids 764 to 1035 and 1691 to 1905 of SEQ ID No. 1 but not amino acids 2255 to 2645 of SEQ ID NO 1.

According to the present invention, a Factor VIII preparation comprising Von Willebrand Factor peptides is provided. Factor VIII form a complex with the comprising Von Willebrand Factor peptides.

Factor VIII as used herein covers full-length Factor VIII, B domain deleted Factor VIII or a Factor VIII wherein the B domain has been replaced by an artificial linker or a fragment of the natural B domain or a combination of both, i.e. the B-domain has a different size compared to full-length Factor VIII. It also covers Factor VIII with a limited number of modifications having insertion, deletion or substitutions, especially Factor VIII adapted to haplotypes as described in K. R. Viel, et al. New England J Med 2009; 360:1618-1627. Preferably, the sequence homology to Factor VIII (as defined in amino acids 20-2351 of P00451 of SwissProt Jul. 21, 1986) but disregarding the homology in the B-Domain of 99% according to FASTA as implemented in FASTA version 36, based on W. R. Pearson (1996) "Effective protein sequence comparison" Meth. Enzymol. 266:227-258. In other words, when calculating a sequence homology, the B-domain is not included in the comparison of both proteins. Also covered is modified Factor VIII, like HES-Factor VIII or PEG Factor VIII or Factor VIII Fc fusion proteins and Factor VIII albumin fusion proteins as described in Oldenburg, Haemophilia (2014), 20 (Suppl. 4), 23-28.

The Factor VIII of the present invention may be plasma derived or recombinant Factor VIII. When recombinant Factor VIII is used, it is preferably expressed in a human cell line to mimic human glycosylation pattern (Casademunt, Eur J Haematol. 2012; 89:165-76) or as described in WO 2010/020690.

Von Willebrand Factor peptides as used herein are peptides comprising at least amino acids 764 to 1035 of SEQ ID No. 1 and 1691 to 1905 of SEQ ID No. 1 in a single amino acid chain. These amino acids may be part of a longer sequence comprising both of these sequences together. In other words, the Von Willebrand peptides of the invention comprise both SEQ ID No. 5 and SEQ ID No. 6. They may comprise further parts of Von Willebrand Factor, excluding all the amino acids 2255 to 2645 (SEQ ID No. 7). The Von Willebrand peptides may comprise other sequences that are part of SEQ ID No. 1 or sequences that are not part of SEQ ID No. 1, e.g. amino acid linkers or the like. Preferably, the total amount of amino acids that are not part of SEQ ID No. 1 is not more than 50, not more than 20 or not more than 10 amino acids.

One important aspect of the invention is that amino acids 2255 to 2645 of SEQ ID No. 1 are not part of the Von Willebrand Factor peptides. In other words, the Von Willebrand Factor peptides do not comprise any sequence that has at least 90% homology to SEQ ID No. 7 according to FASTA, described below.

SEQ ID No. 1 is sequence P04275 of Swiss Prot database as of Jan. 11, 2011.

The Von Willebrand Factor peptides in the composition of the present invention may be peptides having the same sequence or may be a mixture of peptides having sequences as defined above.

Typically a molecular ratio of Factor VIII and Von Willebrand Factor peptides will be between 1:1 and 1:20, preferably 1:2 to 1:10. If the Von Willebrand factor peptides are in the form of dimers or multimers, the molecular ratio is calculated on a single amino acid chain, i.e. a complex of a Factor VIII molecule with a dimer of Von Willebrand factor peptides will have a ratio of 1:2.

A complex, as used herein refers to a non-covalent binding of Factor VIII to one or more Von Willebrand Factor peptides.

In a preferred embodiment of the invention, the Von Willebrand Factor peptides are fragments of Von Willebrand Factor, i.e. N-terminal and/or C-terminal truncated forms of Von Willebrand Factor.

In one embodiment, the fragments comprise amino acids 764 to 1905 of SEQ ID No. 1.

A further embodiment of the invention is a composition comprising a complex of Factor VIII and one or more Von Willebrand Factor peptides that are fragments of Von Willebrand Factor and have an amino acid sequence that corresponds to the amino acid sequence of SEQ ID NO 1 starting form amino acid 764 and ending between amino acid 1905 and 2153 with up to 20, or up to 10 modifications selected from amino acid deletions, amino acid insertions or amino acid substitutions.

Preferred Von Willebrand Factor peptides are:

Peptides having the sequence 764 to 1905 of SEQ ID No. 1

Peptides having the sequence 764 to 1906 of SEQ ID No. 1

Peptides having the sequence 764 to 1907 of SEQ ID No. 1

Peptides having the sequence 764 to 1908 of SEQ ID No. 1

Peptides having the sequence 764 to 1909 of SEQ ID No. 1

Peptides having the sequence 764 to 1910 of SEQ ID No. 1

Peptides having the sequence 764 to 1911 of SEQ ID No. 1

Peptides having the sequence 764 to 1912 of SEQ ID No. 1

Peptides having the sequence 764 to 1913 of SEQ ID No. 1

Peptides having the sequence 764 to 1914 of SEQ ID No. 1

Peptides having the sequence 764 to 1915 of SEQ ID No. 1

Peptides having the sequence 764 to 1916 of SEQ ID No. 1

Peptides having the sequence 764 to 1917 of SEQ ID No. 1

Peptides having the sequence 764 to 1918 of SEQ ID No. 1

Peptides having the sequence 764 to 1919 of SEQ ID No. 1

Peptides having the sequence 764 to 1920 of SEQ ID No. 1

Peptides having the sequence 764 to 1921 of SEQ ID No. 1

Peptides having the sequence 764 to 1922 of SEQ ID No. 1

Peptides having the sequence 764 to 1923 of SEQ ID No. 1

Peptides having the sequence 764 to 1924 of SEQ ID No. 1

Peptides having the sequence 764 to 1925 of SEQ ID No. 1

Peptides having the sequence 764 to 1926 of SEQ ID No. 1

Peptides having the sequence 764 to 1927 of SEQ ID No. 1

Peptides having the sequence 764 to 1928 of SEQ ID No. 1

Peptides having the sequence 764 to 1929 of SEQ ID No. 1

Peptides having the sequence 764 to 1930 of SEQ ID No. 1

Peptides having the sequence 764 to 1931 of SEQ ID No. 1

Peptides having the sequence 764 to 1932 of SEQ ID No. 1

Peptides having the sequence 764 to 1933 of SEQ ID No. 1

Peptides having the sequence 764 to 1934 of SEQ ID No. 1

Peptides having the sequence 764 to 1935 of SEQ ID No. 1

Peptides having the sequence 764 to 1936 of SEQ ID No. 1

Peptides having the sequence 764 to 1937 of SEQ ID No. 1

Peptides having the sequence 764 to 1938 of SEQ ID No. 1

Peptides having the sequence 764 to 1939 of SEQ ID No. 1

Peptides having the sequence 764 to 1940 of SEQ ID No. 1

Peptides having the sequence 764 to 1941 of SEQ ID No. 1

Peptides having the sequence 764 to 1942 of SEQ ID No. 1

Peptides having the sequence 764 to 1943 of SEQ ID No. 1

Peptides having the sequence 764 to 1944 of SEQ ID No. 1

Peptides having the sequence 764 to 1945 of SEQ ID No. 1

Peptides having the sequence 764 to 1946 of SEQ ID No. 1

Peptides having the sequence 764 to 1947 of SEQ ID No. 1

Peptides having the sequence 764 to 1948 of SEQ ID No. 1

Peptides having the sequence 764 to 1949 of SEQ ID No. 1

Peptides having the sequence 764 to 1950 of SEQ ID No. 1

Peptides having the sequence 764 to 1951 of SEQ ID No. 1

Peptides having the sequence 764 to 1952 of SEQ ID No. 1

Peptides having the sequence 764 to 1953 of SEQ ID No. 1

Peptides having the sequence 764 to 1954 of SEQ ID No. 1

Peptides having the sequence 764 to 1955 of SEQ ID No. 1

Peptides having the sequence 764 to 1956 of SEQ ID No. 1

Peptides having the sequence 764 to 1957 of SEQ ID No. 1

Peptides having the sequence 764 to 1958 of SEQ ID No. 1

Peptides having the sequence 764 to 1959 of SEQ ID No. 1

Peptides having the sequence 764 to 1960 of SEQ ID No. 1

Peptides having the sequence 764 to 1961 of SEQ ID No. 1

Peptides having the sequence 764 to 1962 of SEQ ID No. 1

Peptides having the sequence 764 to 1963 of SEQ ID No. 1

Peptides having the sequence 764 to 1964 of SEQ ID No. 1

Peptides having the sequence 764 to 1965 of SEQ ID No. 1

Peptides having the sequence 764 to 1966 of SEQ ID No. 1

Peptides having the sequence 764 to 1967 of SEQ ID No. 1

Peptides having the sequence 764 to 1968 of SEQ ID No. 1

Peptides having the sequence 764 to 1969 of SEQ ID No. 1

Peptides having the sequence 764 to 1970 of SEQ ID No. 1

Peptides having the sequence 764 to 1971 of SEQ ID No. 1

Peptides having the sequence 764 to 1972 of SEQ ID No. 1

Peptides having the sequence 764 to 1973 of SEQ ID No. 1

Peptides having the sequence 764 to 1974 of SEQ ID No. 1

Peptides having the sequence 764 to 1975 of SEQ ID No. 1

Peptides having the sequence 764 to 1976 of SEQ ID No. 1

Peptides having the sequence 764 to 1977 of SEQ ID No. 1

Peptides having the sequence 764 to 1978 of SEQ ID No. 1

Peptides having the sequence 764 to 1979 of SEQ ID No. 1

Peptides having the sequence 764 to 1980 of SEQ ID No. 1

Peptides having the sequence 764 to 1981 of SEQ ID No. 1

Peptides having the sequence 764 to 1982 of SEQ ID No. 1

Peptides having the sequence 764 to 1983 of SEQ ID No. 1

Peptides having the sequence 764 to 1984 of SEQ ID No. 1

Peptides having the sequence 764 to 1985 of SEQ ID No. 1

Peptides having the sequence 764 to 1986 of SEQ ID No. 1

Peptides having the sequence 764 to 1987 of SEQ ID No. 1

Peptides having the sequence 764 to 1988 of SEQ ID No. 1

Peptides having the sequence 764 to 1989 of SEQ ID No. 1

Peptides having the sequence 764 to 1990 of SEQ ID No. 1

Peptides having the sequence 764 to 1991 of SEQ ID No. 1
Peptides having the sequence 764 to 1992 of SEQ ID No. 1
Peptides having the sequence 764 to 1993 of SEQ ID No. 1
Peptides having the sequence 764 to 1994 of SEQ ID No. 1
Peptides having the sequence 764 to 1995 of SEQ ID No. 1
Peptides having the sequence 764 to 1996 of SEQ ID No. 1
Peptides having the sequence 764 to 1997 of SEQ ID No. 1
Peptides having the sequence 764 to 1998 of SEQ ID No. 1
Peptides having the sequence 764 to 1999 of SEQ ID No. 1
Peptides having the sequence 764 to 2000 of SEQ ID No. 1
Peptides having the sequence 764 to 2001 of SEQ ID No. 1
Peptides having the sequence 764 to 2002 of SEQ ID No. 1
Peptides having the sequence 764 to 2003 of SEQ ID No. 1
Peptides having the sequence 764 to 2004 of SEQ ID No. 1
Peptides having the sequence 764 to 2005 of SEQ ID No. 1
Peptides having the sequence 764 to 2006 of SEQ ID No. 1
Peptides having the sequence 764 to 2007 of SEQ ID No. 1
Peptides having the sequence 764 to 2008 of SEQ ID No. 1
Peptides having the sequence 764 to 2009 of SEQ ID No. 1
Peptides having the sequence 764 to 2010 of SEQ ID No. 1.
Peptides having the sequence 764 to 2011 of SEQ ID No. 1
Peptides having the sequence 764 to 2012 of SEQ ID No. 1
Peptides having the sequence 764 to 2013 of SEQ ID No. 1
Peptides having the sequence 764 to 2014 of SEQ ID No. 1
Peptides having the sequence 764 to 2015 of SEQ ID No. 1
Peptides having the sequence 764 to 2016 of SEQ ID No. 1
Peptides having the sequence 764 to 2017 of SEQ ID No. 1
Peptides having the sequence 764 to 2018 of SEQ ID No. 1
Peptides having the sequence 764 to 2019 of SEQ ID No. 1
Peptides having the sequence 764 to 2020 of SEQ ID No. 1
Peptides having the sequence 764 to 2021 of SEQ ID No. 1
Peptides having the sequence 764 to 2022 of SEQ ID No. 1
Peptides having the sequence 764 to 2023 of SEQ ID No. 1
Peptides having the sequence 764 to 2024 of SEQ ID No. 1
Peptides having the sequence 764 to 2025 of SEQ ID No. 1
Peptides having the sequence 764 to 2026 of SEQ ID No. 1
Peptides having the sequence 764 to 2027 of SEQ ID No. 1
Peptides having the sequence 764 to 2028 of SEQ ID No. 1
Peptides having the sequence 764 to 2029 of SEQ ID No. 1
Peptides having the sequence 764 to 2030 of SEQ ID No. 1
Peptides having the sequence 764 to 2031 of SEQ ID No. 1
Peptides having the sequence 764 to 2032 of SEQ ID No. 1
Peptides having the sequence 764 to 2033 of SEQ ID No. 1
Peptides having the sequence 764 to 2034 of SEQ ID No. 1
Peptides having the sequence 764 to 2035 of SEQ ID No. 1
Peptides having the sequence 764 to 2036 of SEQ ID No. 1
Peptides having the sequence 764 to 2037 of SEQ ID No. 1
Peptides having the sequence 764 to 2038 of SEQ ID No. 1
Peptides having the sequence 764 to 2039 of SEQ ID No. 1
Peptides having the sequence 764 to 2040 of SEQ ID No. 1
Peptides having the sequence 764 to 2041 of SEQ ID No. 1
Peptides having the sequence 764 to 2042 of SEQ ID No. 1
Peptides having the sequence 764 to 2043 of SEQ ID No. 1
Peptides having the sequence 764 to 2044 of SEQ ID No. 1
Peptides having the sequence 764 to 2045 of SEQ ID No. 1
Peptides having the sequence 764 to 2046 of SEQ ID No. 1
Peptides having the sequence 764 to 2047 of SEQ ID No. 1
Peptides having the sequence 764 to 2048 of SEQ ID No. 1
Peptides having the sequence 764 to 2049 of SEQ ID No. 1
Peptides having the sequence 764 to 2050 of SEQ ID No. 1
Peptides having the sequence 764 to 2051 of SEQ ID No. 1
Peptides having the sequence 764 to 2052 of SEQ ID No. 1
Peptides having the sequence 764 to 2053 of SEQ ID No. 1
Peptides having the sequence 764 to 2054 of SEQ ID No. 1
Peptides having the sequence 764 to 2055 of SEQ ID No. 1
Peptides having the sequence 764 to 2056 of SEQ ID No. 1

Peptides having the sequence 764 to 2057 of SEQ ID No. 1
Peptides having the sequence 764 to 2058 of SEQ ID No. 1
Peptides having the sequence 764 to 2059 of SEQ ID No. 1
Peptides having the sequence 764 to 2060 of SEQ ID No. 1
Peptides having the sequence 764 to 2061 of SEQ ID No. 1
Peptides having the sequence 764 to 2062 of SEQ ID No. 1
Peptides having the sequence 764 to 2063 of SEQ ID No. 1
Peptides having the sequence 764 to 2064 of SEQ ID No. 1
Peptides having the sequence 764 to 2065 of SEQ ID No. 1
Peptides having the sequence 764 to 2066 of SEQ ID No. 1
Peptides having the sequence 764 to 2067 of SEQ ID No. 1
Peptides having the sequence 764 to 2068 of SEQ ID No. 1
Peptides having the sequence 764 to 2069 of SEQ ID No. 1
Peptides having the sequence 764 to 2070 of SEQ ID No. 1
Peptides having the sequence 764 to 2071 of SEQ ID No. 1
Peptides having the sequence 764 to 2072 of SEQ ID No. 1
Peptides having the sequence 764 to 2073 of SEQ ID No. 1
Peptides having the sequence 764 to 2074 of SEQ ID No. 1
Peptides having the sequence 764 to 2075 of SEQ ID No. 1
Peptides having the sequence 764 to 2076 of SEQ ID No. 1
Peptides having the sequence 764 to 2077 of SEQ ID No. 1
Peptides having the sequence 764 to 2078 of SEQ ID No. 1
Peptides having the sequence 764 to 2079 of SEQ ID No. 1
Peptides having the sequence 764 to 2080 of SEQ ID No. 1
Peptides having the sequence 764 to 2081 of SEQ ID No. 1
Peptides having the sequence 764 to 2082 of SEQ ID No. 1
Peptides having the sequence 764 to 2083 of SEQ ID No. 1
Peptides having the sequence 764 to 2084 of SEQ ID No. 1
Peptides having the sequence 764 to 2085 of SEQ ID No. 1
Peptides having the sequence 764 to 2086 of SEQ ID No. 1
Peptides having the sequence 764 to 2087 of SEQ ID No. 1
Peptides having the sequence 764 to 2088 of SEQ ID No. 1
Peptides having the sequence 764 to 2089 of SEQ ID No. 1
Peptides having the sequence 764 to 2090 of SEQ ID No. 1
Peptides having the sequence 764 to 2091 of SEQ ID No. 1
Peptides having the sequence 764 to 2092 of SEQ ID No. 1
Peptides having the sequence 764 to 2093 of SEQ ID No. 1
Peptides having the sequence 764 to 2094 of SEQ ID No. 1
Peptides having the sequence 764 to 2095 of SEQ ID No. 1
Peptides having the sequence 764 to 2096 of SEQ ID No. 1
Peptides having the sequence 764 to 2097 of SEQ ID No. 1
Peptides having the sequence 764 to 2098 of SEQ ID No. 1
Peptides having the sequence 764 to 2099 of SEQ ID No. 1
Peptides having the sequence 764 to 2100 of SEQ ID No. 1
Peptides having the sequence 764 to 2101 of SEQ ID No. 1
Peptides having the sequence 764 to 2102 of SEQ ID No. 1
Peptides having the sequence 764 to 2103 of SEQ ID No. 1
Peptides having the sequence 764 to 2104 of SEQ ID No. 1
Peptides having the sequence 764 to 2105 of SEQ ID No. 1
Peptides having the sequence 764 to 2106 of SEQ ID No. 1
Peptides having the sequence 764 to 2107 of SEQ ID No. 1
Peptides having the sequence 764 to 2108 of SEQ ID No. 1
Peptides having the sequence 764 to 2109 of SEQ ID No. 1
Peptides having the sequence 764 to 2110 of SEQ ID No. 1
Peptides having the sequence 764 to 2111 of SEQ ID No. 1
Peptides having the sequence 764 to 2112 of SEQ ID No. 1
Peptides having the sequence 764 to 2113 of SEQ ID No. 1
Peptides having the sequence 764 to 2114 of SEQ ID No. 1
Peptides having the sequence 764 to 2115 of SEQ ID No. 1
Peptides having the sequence 764 to 2116 of SEQ ID No. 1
Peptides having the sequence 764 to 2117 of SEQ ID No. 1
Peptides having the sequence 764 to 2118 of SEQ ID No. 1
Peptides having the sequence 764 to 2119 of SEQ ID No. 1
Peptides having the sequence 764 to 2120 of SEQ ID No. 1
Peptides having the sequence 764 to 2121 of SEQ ID No. 1
Peptides having the sequence 764 to 2122 of SEQ ID No. 1

Peptides having the sequence 764 to 2123 of SEQ ID No. 1
Peptides having the sequence 764 to 2124 of SEQ ID No. 1
Peptides having the sequence 764 to 2125 of SEQ ID No. 1
Peptides having the sequence 764 to 2126 of SEQ ID No. 1
Peptides having the sequence 764 to 2127 of SEQ ID No. 1
Peptides having the sequence 764 to 2128 of SEQ ID No. 1
Peptides having the sequence 764 to 2129 of SEQ ID No. 1
Peptides having the sequence 764 to 2130 of SEQ ID No. 1
Peptides having the sequence 764 to 2131 of SEQ ID No. 1
Peptides having the sequence 764 to 2132 of SEQ ID No. 1
Peptides having the sequence 764 to 2133 of SEQ ID No. 1
Peptides having the sequence 764 to 2134 of SEQ ID No. 1
Peptides having the sequence 764 to 2135 of SEQ ID No. 1.
Peptides having the sequence 764 to 2136 of SEQ ID No. 1
Peptides having the sequence 764 to 2137 of SEQ ID No. 1
Peptides having the sequence 764 to 2138 of SEQ ID No. 1
Peptides having the sequence 764 to 2139 of SEQ ID No. 1
Peptides having the sequence 764 to 2140 of SEQ ID No. 1
Peptides having the sequence 764 to 2141 of SEQ ID No. 1
Peptides having the sequence 764 to 2142 of SEQ ID No. 1
Peptides having the sequence 764 to 2143 of SEQ ID No. 1
Peptides having the sequence 764 to 2144 of SEQ ID No. 1
Peptides having the sequence 764 to 2145 of SEQ ID No. 1
Peptides having the sequence 764 to 2146 of SEQ ID No. 1
Peptides having the sequence 764 to 2147 of SEQ ID No. 1
Peptides having the sequence 764 to 2148 of SEQ ID No. 1
Peptides having the sequence 764 to 2149 of SEQ ID No. 1
Peptides having the sequence 764 to 2150 of SEQ ID No. 1
Peptides having the sequence 764 to 2151 of SEQ ID No. 1
Peptides having the sequence 764 to 2152 of SEQ ID No. 1
Peptides having the sequence 764 to 2153 of SEQ ID No. 1

A further embodiment of the invention is a composition comprising a complex of Factor VIII with one or more Von Willebrand Factor peptides, wherein
the Von Willebrand factor peptides are fragments of Von Willebrand Factor the complex of Factor VIII and the fragments of Von Willebrand Factor show a reduced binding to phospholipid membranes compared to Factor VIII alone
the complex of Factor VIII and the fragments of Von Willebrand Factor show a reduced binding to collagen III compared to the complex of Factor VIII and full length Von Willebrand Factor
the complex of Factor VIII and the fragments of Von Willebrand Factor show a reduced binding to heparin compared to the complex of Factor VIII and full length Von Willebrand Factor.

Preferably, the Von Willebrand Factor peptides have a molecular weight <500 kD, preferably <400 kD. As the Von Willebrand Factor often forms oligomers or multimers, also the peptides of the present invention may be in the form of multimers or oligomers.

In a preferred embodiment the peptides of the present invention have at least one property selected from the group consisting of
(i) an affinity binding constant for heparin of $K_D$>1 nM, preferably ≥2.43 nM
(ii) an affinity binding constant for collagen III of $K_D$>5 nM, preferably ≥17.02 nM
(iii) an affinity binding constant for Factor VIII of $K_D$<100 nM or <10 nM, preferably ≤6.19 nM and
(iv) an inhibition of Factor VIII phospholipid binding of at least 70%, preferably at least 80% or at least 90%.

The Von Willebrand factor peptides of the invention show preferably a reduced binding to heparin, a lower affinity for collagen (like collagen III), a lower affinity to phospholipids but still a high binding to Factor VIII.

Surprisingly, low binding to phospholipids and collagen improves release rate in case of non-intravenous administration, especially subcutaneous.

The measurement of the respective affinity binding constants is described in the experimental part.

In one embodiment, the Von Willebrand Factor peptides are derived from Von Willebrand Factor by proteolytic or chemical cleavage. If proteolytic cleavage is used, S. aureus V-8 protease is especially preferred.

Preferably, the composition of the present invention has at least one of the following properties:
(i) the Von Willebrand Factor peptides shield Factor VIII from antibody binding to minimize inhibitor formation in a patient
(ii) stabilises Factor VIII to provide a remaining Factor VIII activity of at least 90% after storage for 12 month in a frozen liquid form at −70° C.
(iii) stabilises Factor VIII to provide a remaining Factor VIII activity of at least 90% after storage for 24 month in a freeze-dried form at 5° C.
(iv) stabilises Factor VIII to provide a remaining Factor VIII activity of at least 90% after storage for 12 month in a freeze-dried form at 25° C.
(v) prolonges half-life of Factor VIII in-vivo by at least 20% and
(vi) reduces inhibitor formation in previously untreated patients to less than 20%, preferably less than 10% after treatment with the composition for 6 months.

Surprisingly, the Von Willebrand Factor peptides seem to increase stability of Factor upon storage (shelf-life) and/or reduce inhibitor formation in patients. Inhibitor formation is one of the major problems in the treatment of chronic bleeding disorders.

The composition of the present invention is especially useful in the treatment or prevention of a bleeding disorder.

Therefore, a further embodiment of the invention is a method of treating a bleeding disorder comprising administering to a patient in need thereof an effective amount of the composition of the present invention.

The amount depends on the disease or condition to be treated and may be selected by a person skilled in the art. For long term treatment, amounts of 20 to 40 IU/kg bodyweight per application are typically suitable. In an emergency situation, the amount may be about 10 to 50 IU/kg bodyweight.

The composition of the invention may be applied by intravenous administration or non-intravenous administration. The non-intravenous administration may be a subcutaneous injection, an intradermal injection or an intramuscular administration.

One advantage of the method of the present invention is the possibility to use nano filtration for virus removal. Von Willebrand Factor, because of its size, may not be nanofiltrated with a nanofilter with a small pore size to remove viruses. Because the Von Willebrand Factor peptides are much smaller in size than the full length Von Willebrand Factor molecule, nanofiltration with small pore sizes becomes possible. Nanofiltration is done at a pore size and conditions that reduces the concentration of one of the smallest known viruses porcine parvovirus by a least a factor of 100 (2 log), preferably by at least a factor 1000 (3 log) and most preferably to a concentration below detection limit of the parvovirus assay, optionally using one or more nanofilters in series. For this test, porcine parvovirus is spiked in a sample and analysed after filtration.

Therefore, a further embodiment of the invention is a method for virus reduction comprising the step of nanofiltrating the Von Willebrand Factor peptides prior or after a combination with Factor VIII, whereby porcine parvovirus would be reduced by at least 2 log.

A preferred puffer for administration of the composition of the invention comprises melizitose, preferably in an amount of up to 1,000 mM particularly from about 10 mM to about 200 mM, in particular from about 10 mM to about 100 mM.

A further embodiment of the invention is a method of preparing Von Willebrand Factor peptides comprising the following steps:
Incubating Von Willebrand Factor with *S. aureus* V-8 protease for 2 to 16 hours at an enzyme to Von Willebrand Factor weight/weight ratio of 1:5 to 1:100
Binding and purifying on an anion exchanger and collecting the desired purified vWF peptides in a fraction coming from the anion exchanger by applying an increased amount of salt concentration.

EXAMPLES

The invention is further explained by the following, non-limiting examples.

Example 1

Production and Purification of Fragments Derived from Plasmatic Von Willebrand Factor.

Production and Purification of Fragment III (SPIII, Res. 764-2128)

(According to Marti et al. Identification of disulfide-bridged substructures within human von Willebrand factor. Biochemistry 1987; 26:8099-8109 with modifications) (SEQ. ID. No. 2):

SLSCRPPMVKLVCPADNLRAEGLECTKTCQNYDLECMSMGCVSGCLCPPG

MVRHENRCVA

LERCPCFHQGKEYAPGETVKIGCNTCVCQDRKWNCTDHVCDATCSTIGMA

HYLTFDGLKY

LFPGECQYVLVQDYCGSNPGTFRILVGNKGCSHPSVKCKKRVTILVEGGE

IELFDGEVNV

KRPMKDETHFEVVESGRYIILLLGKALSVVWDRHLSISVVLKQTYQEKVC

GLCGNFDGIQ

NNDLTSSNLQVEEDPVDFGNSWKVSSQCADTRKVPLDSSPATCHNNIMKQ

TMVDSSCRIL

TSDVFQDCNKLVDPEPYLDVCIYDTCSCESIGDCACFCDTIAAYAHVCAQ

HGKVVTWRTA

TLCPQSCEERNLRENGYECEWRYNSCAPACQVTCQHPEPLACPVQCVEGC

HAHCPPGKIL

DELLQTCVDPEDCPVCEVAGRRFASGKKVTLNPSDPEHCQICHCDVVNLT

CEACQEPGGL

VVPPTDAPVSPTTLYVEDISEPPLHDFYCSRLLDLVFLLDGSSRLSEAEF

EVLKAFVVDM

-continued

MERLRISQKWVRVAVVEYHDGSHAYIGLKDRKRPSELRRIASQVKYAGSQ

VASTSEVLKY

TLFQIFSKIDRPEASRITLLLMASQEPQRMSRNFVRYVQGLKKKKVIVIP

VGIGPHANLK

QIRLIEKQAPENKAFVLSSVDELEQQRDEIVSYLCDLAPEAPPPTLPPDM

AQVTVGPGLL

GVSTLGPKRNSMVLDVAFVLEGSDKIGEADFNRSKEFMEEVIQRMDVGQD

SIHVTVLQYS

YMVTVEYPFSEAQSKGDILQRVREIRYQGGNRTNTGLALRYLSDHSFLVS

QGDREQAPNL

VYMVTGNPASDEIKRLPGDIQVVPIGVGPNANVQELERIGWPNAPILIQD

FETLPREAPD

LVLQRCCSGEGLQIPTLSPAPDCSQPLDVILLLDGSSSFPASYFDEMKSF

AKAFISKANI

GPRLTQVSVLQYGSITTIDVPWNVVPEKAHLLSLVDVMQREGGPSQIGDA

LGFAVRYLTS

EMHGARPGASKAVVILVTDVSVDSVDAAADAARSNRVTVFPIGIGDRYDA

AQLRILAGPA

GDSNVVKLQRIEDLPTMVTLGNSFLHKLCSGFVRICMDEDGNEKRPGDVW

TLPDQCHTVT

CQPDGQTLLKSHRVNCDRGLRPSCPNSQSPVKVEETCGCRWTCPCVCTGS

STRHIVTFDG

QNFKLTGSCSYVLFQNKEQDLEVILHNGACSPGARQGCMKSIEVKHSALS

VELHSDMEVT

VNGRLVSVPYVGGNMEVNVYGAIMHEVRFNHLGHIFTFTPQNNEFQLQLS

PKTFASKTYG

LCGICDENGANDFMLRDGTVTTDWKTLVQEWTVQRPGQTCQPILE

Fragment III is prepared by digestion of plasma derived Von Willebrand Factor (pdVWF) with S. aureus V-8 protease. The digestion is carried out for 3 hours at 37° C. in a 50 mM Tris-HCl, 150 mM NaCl pH 7.8 buffer at a 1:40 enzyme to protein weight ratio.

Figure 1:
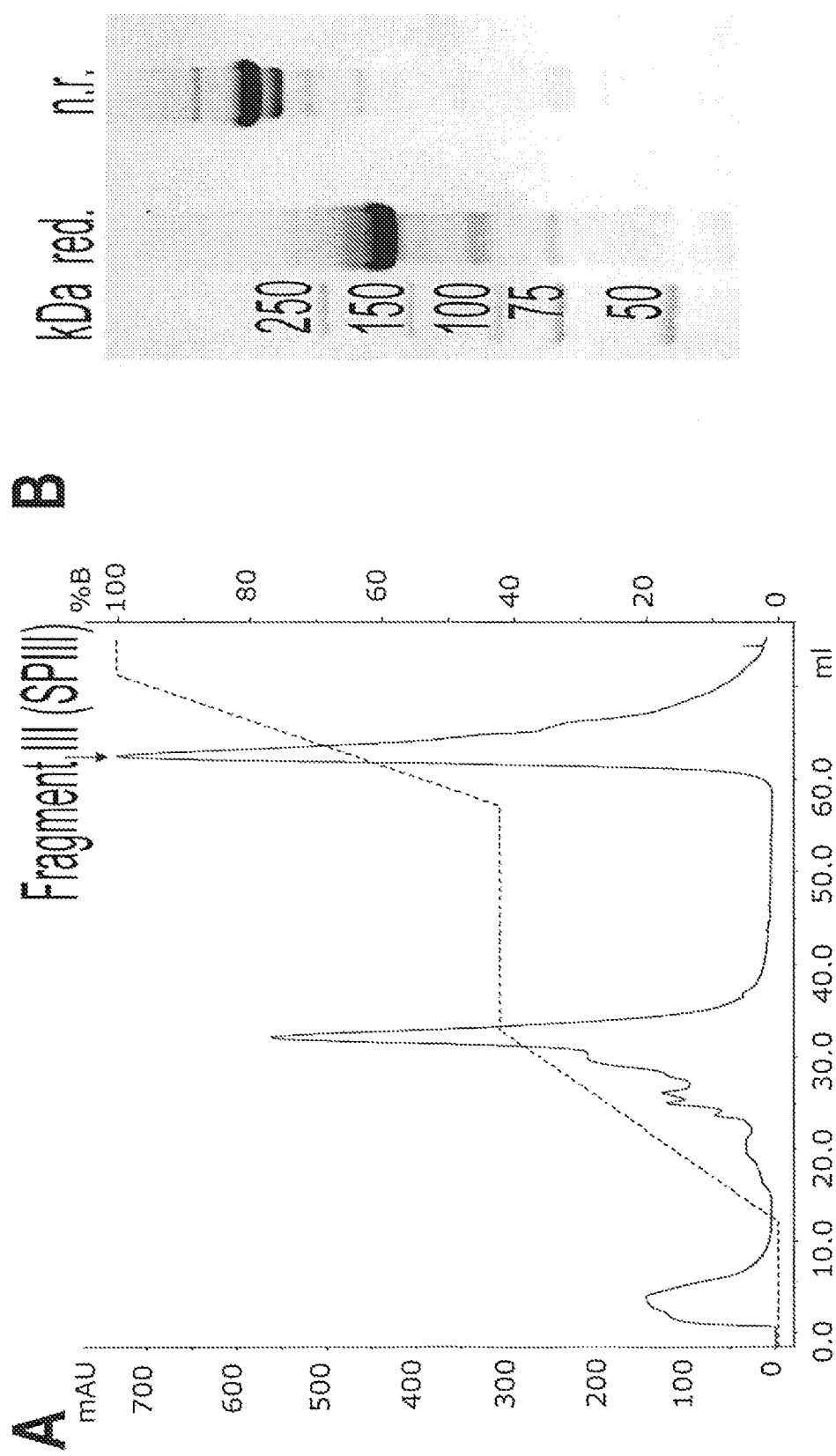
FIG. 1 shows purification of the fragment III (SPIII) from pdVWF digested by *S. aureus* V8 protease. A—MonoQ chromatogram of elution profile of the fragment III (indicated by an arrow). B—SDS-PAGE gel of the purified fragment; red.—reduced; n.r.—non-reduced.

The purification of the fragment is carried out using a strong anion exchange column (MonoQ). The running buffer is a 20 mM Tris-HCl pH 7.4, and the elution buffer (buffer B) is 20 mM Tris-HCl, 500 mM NaCl pH 7.4. The S. aureus V-8 protease elutes from the anion exchange column at ca. 22 mS/cm (ca. 40% buffer B), therefore long washing step at 42% prior to elution of the fragment is required to wash out the protease. Alternatively an SEC step on Superose 6 10/300 GL can be conducted for protease removal. The fragment III purification and the product obtained are depicted on FIG. 1. The sequence defined by Marti et al. 1987 has been confirmed by MS analysis.

Production and Purification of Fragment I (III-T4, Res. 764-1035)

(According to Marti et al. 1987 with modifications) (SEQ. ID. No. 3):

```
SLSCRPPMVKLVCPADNLRAEGLECTKTCQNYDLECMSMGCVSGCLCPPG
MVRHENRCVA
LERCPCFHQGKEYAPGETVKIGCNTCVCQDRKWNCTDHVCDATCSTIGMA
HYLTFDGLKY
LFPGECQYVLVQDYCGSNPGTFRILVGNKGCSHPSVKCKKRVTILVEGGE
IELFDGEVNV
KRPMKDETHFEVVESGRYIILLLGKALSVVWDRHLSISVVLKQTYQEKVC
GLCGNFDGIQ
NNDLTSSNLQVEEDPVDFGNSWKVSSQCADTR
```

Figure 2:
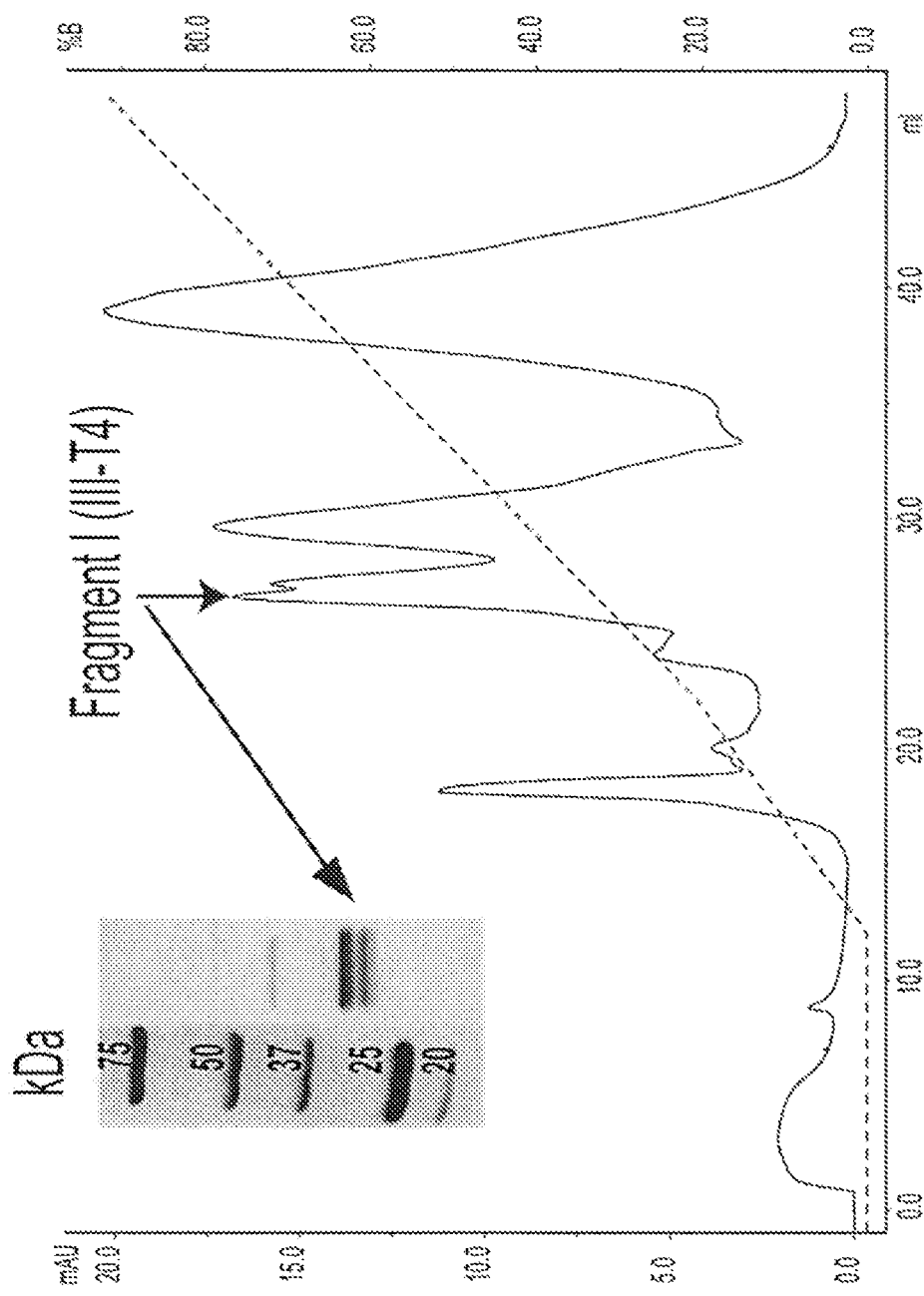
FIG. 2 shows purification of the fragment I (III-T4) from fragment III digested by trypsin. MonoQ chromatogram of elution profile of the fragment I (indicated by an arrow). The non-reducing SDS-PAGE picture of the purified fragment is shown in the insert.

Fragment I is prepared from fragment III (SPIII) by trypsin (TPCK treated from bovine) digestion. The digestion is carried out for 1.5 hours in a 100 mM NH$_4$HCO$_3$ pH 8.0 buffer at a 1:100 enzyme to protein weight ratio. The digestion was terminated by the addition of soybean trypsin inhibitor. The purification of the fragment I is carried out using a strong anion exchange column (MonoQ) followed by SEC on Superose 6, 10/300 GL. The running buffer for the anion exchange column is 20 mM Tris-HCl pH 7.4, and the elution buffer (buffer B) is 20 mM Tris-HCl, 500 mM NaCl pH 7.4. The running buffer for the SEC is PBS (phosphate buffered saline) pH 7.0. The fragment I purification and the product obtained is depicted on FIG. 2. The sequence defined by Marti et al. 1987 has been confirmed by MS analysis.

Production and Purification of Fragment II (Res. 764-1673) (SEQ. ID. No. 4):

```
SLSCRPPMVKLVCPADNLRAEGLECTKTCQNYDLECMSMGCVSGCLCPPG
MVRHENRCVA
LERCPCFHQGKEYAPGETVKIGCNTCVCQDRKWNCTDHVCDATCSTIGMA
HYLTFDGLKY
LFPGECQYVLVQDYCGSNPGTFRILVGNKGCSHPSVKCKKRVTILVEGGE
IELFDGEVNV
KRPMKDETHFEVVESGRYIILLLGKALSVVWDRHLSISVVLKQTYQEKVC
GLCGNFDGIQ
NNDLTSSNLQVEEDPVDFGNSWKVSSQCADTRKVPLDSSPATCHNNIMKQ
TMVDSSCRIL
TSDVFQDCNKLVDPEPYLDVCIYDTCSCESIGDCACFCDTIAAYAHVCAQ
HGKVVTWRTA
TLCPQSCEERNLRENGYECEWRYNSCAPACQVTCQHPEPLACPVQCVEGC
HAHCPPGKIL
DELLQTCVDPEDCPVCEVAGRRFASGKKVTLNPSDPEHCQICHCDVVNLT
CEACQEPGGL
VVPPTDAPVSPTTLYVEDISEPPLHDFYCSRLLDLVFLLDGSSRLSEAEF
EVLKAFVVDM
MERLRISQKWVRVAVVEYHDGSHAYIGLKDRKRPSELRRIASQVKYAGSQ
VASTSEVLKY
TLFQIFSKIDRPEASRITLLLMASQEPQRMSRNFVRYVQGLKKKKVIVIP
VGIGPHANLK
QIRLIEKQAPENKAFVLSSVDELEQQRDEIVSYLCDLAPEAPPPTLPPDM
AQVTVGPGLL
GVSTLGPKRNSMVLDVAFVLEGSDKIGEADFNRSKEFMEEVIQRMDVGQD
SIHVTVLQYS
YMVTVEYPFSEAQSKGDILQRVREIRYQGGNRTNTGLALRYLSDHSFLVS
QGDREQAPNL
VYMVTGNPASDEIKRLPGDIQVVPIGVGPNANVQELERIGWPNAPILIQD
FETLPREAPD
LVLQRCCSGE
```

Fragment II is prepared from fragment III by second *S. aureus* V8 protease digestion. The digestion is carried out for 21 hours in a 50 mM Tris-HCl, 150 mM NaCl pH 7.8 buffer in a 1:10 enzyme to protein weight ratio. The purification of the fragment II is carried out using a strong anion exchange column (MonoQ). The running buffer is a 20 mM Tris-HCl pH 7.4, and the elution buffer (buffer B) is 20 mM Tris-HCl, 500 mM NaCl pH 7.4. A second MonoQ purification with a long washing step at 42% B was required to remove the protease.

Figure 3:
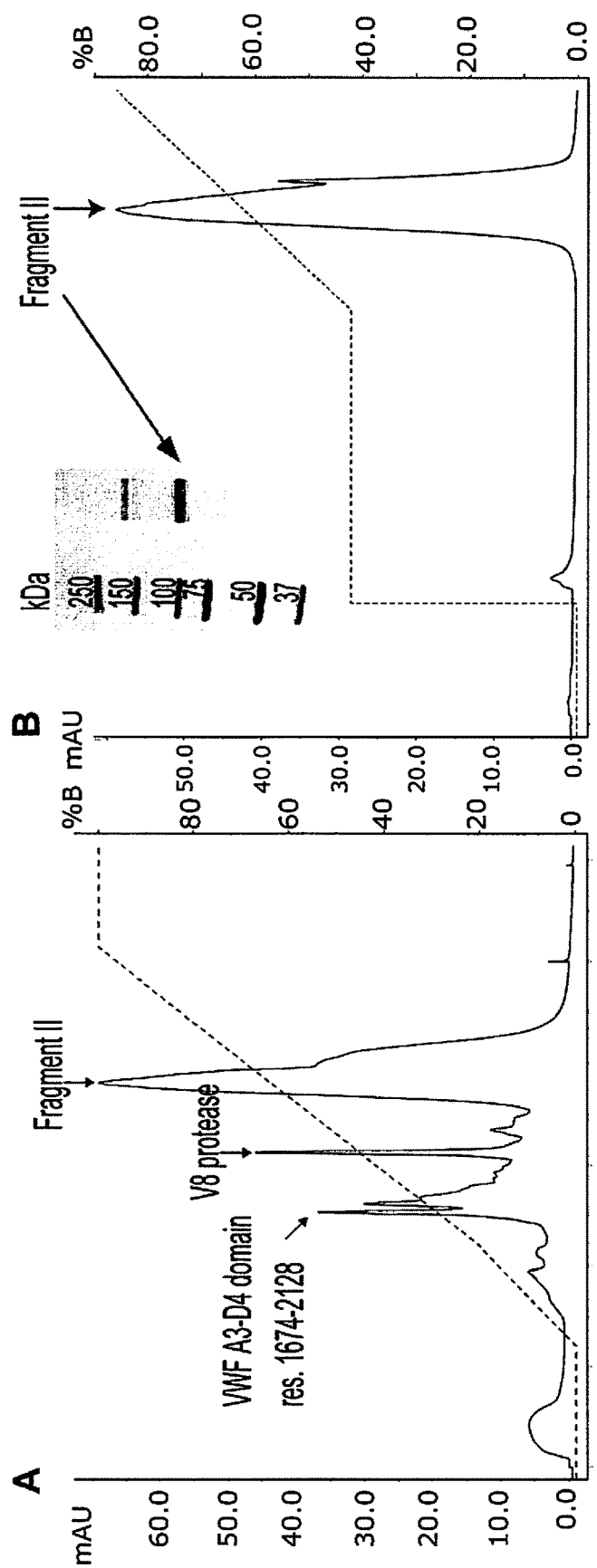
FIG. 3 shows purification of the fragment II from fragment III after second *S. aureus* V8 protease digestion. A—MonoQ chromatogram of elution profile of the fragment II (indicated by an arrow), the second cleavage product as well as the V8 protease are also indicated. B—Chromatogram of the second MonoQ chromatography required for complete removal of the protease. The reducing SDS-PAGE picture of the purified fragment is shown in the insert.

The fragment II purification and the product obtained are depicted on FIG. 3. The second V8 cleavage site between Glu$^{1673}$-Gly$^{1674}$ was determined by Fretto et al. 1986 and confirmed by MS analysis.

Example 2

Determination of Factor VIII Binding Affinity.

Figure 4:
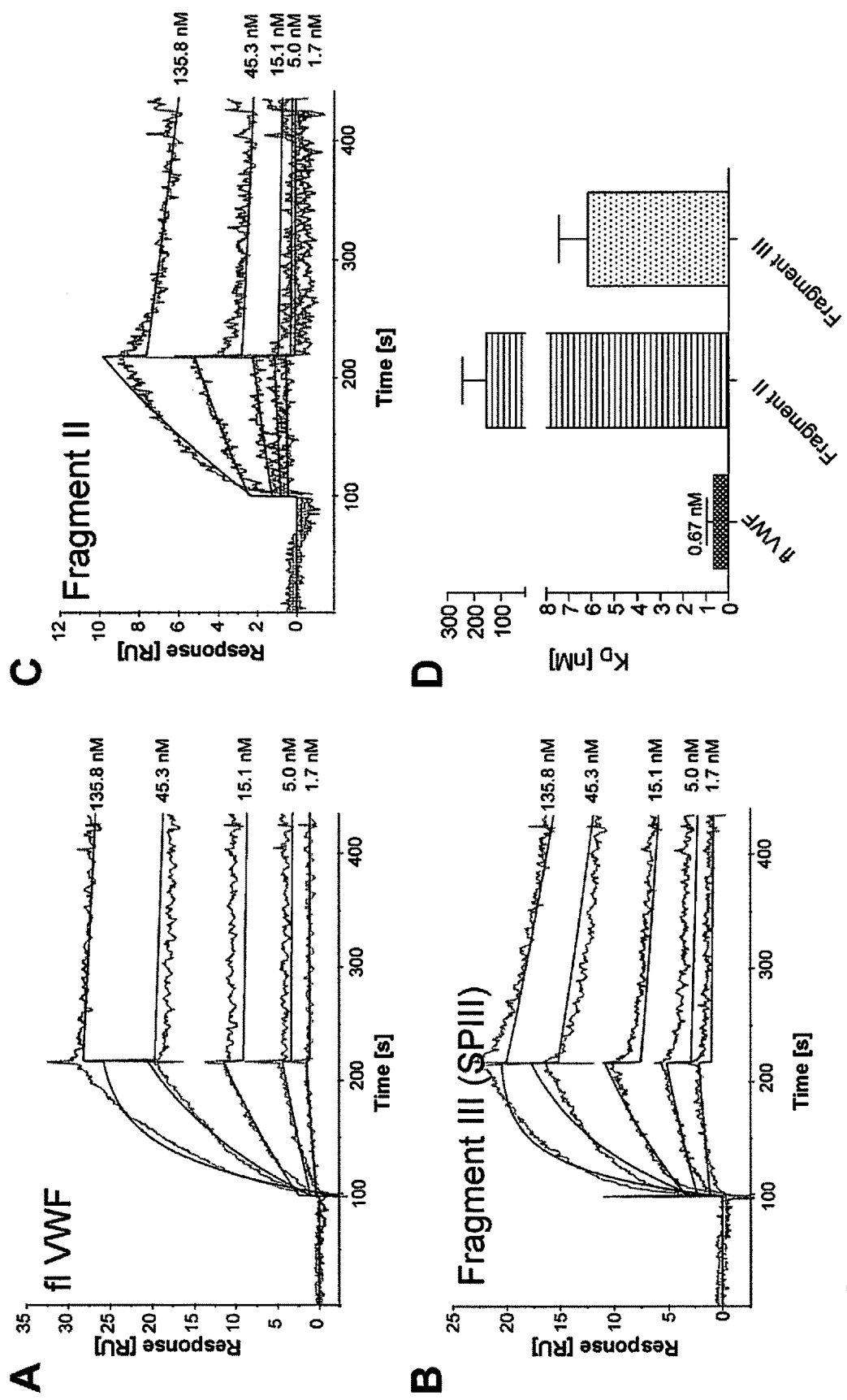
FIG. 4 shows binding of pdVWF, fragment II and III to rFVIII. A, B, C-Binding sensorgrams (grey curves), and curve alignment (black curves) representative for the interaction between immobilized rFVIII and pdVWF/purified fragments II and III. The concentrations and sample type are indicated on the diagram. C—Dissociation constants ($K_D$) expressed as mean and SEM; n=8.

The analysis was carried out using Biacore 2000 instrument (GE Healthcare) according to McCormick et al. 2004 with modifications. Briefly rFVIII was covalently coupled to CM5 Sensor Chip resulting in a ~200 RU coating level. Subsequently the Von Willebrand Factor-fragments as well as full length Von Willebrand Factor (flvWF) were injected over the sensor chip surface. The running buffer was 20 mM HEPES, 150 mM NaCl, 5 mM CaCl$_2$, 0.02% Tween 20. The dissociation affinity constants were determined for flVWF as well as for fragments II and III, there was no significant binding of fragment I to Factor VIII therefore the K$_D$ was not determined. Binding sensorgrams and the calculated K$_D$ values are depicted in FIG. 4. The flVWF bound to rFVIII with K$_D$ of 0.67 nM, fragment III bound with lower affinity (K$_D$ of 6.18 nM), the affinity was further decreased for fragment II (KD of 154.60 nM)

Example 3

Determination of Factor VIII Binding to Phospholipid-Monolayer and Inhibition by Von Willebrand Factor and Von Willebrand Factor-Derived Fragments.

The analysis was carried out using Biacore 2000 instrument (GE Healthcare) according to Saenko et al. 1999 with modifications. Briefly, phospholipid-vesicles were prepared from DOPC (1,2-Dioleoyl-sn-glycerol-3-phosphocholine) and DOPS (1,2-Dioleoyl-sn-glycerol-3-phospho-L-serine). Unilamellar vesicles were prepared according to MacDonal et al. 1991 using an extruder and coated on a HPA sensor chip. Subsequently the compounds of interest were injected over the PCPS surface and the binding level 120 s after injection end was evaluated.

Figure 5:
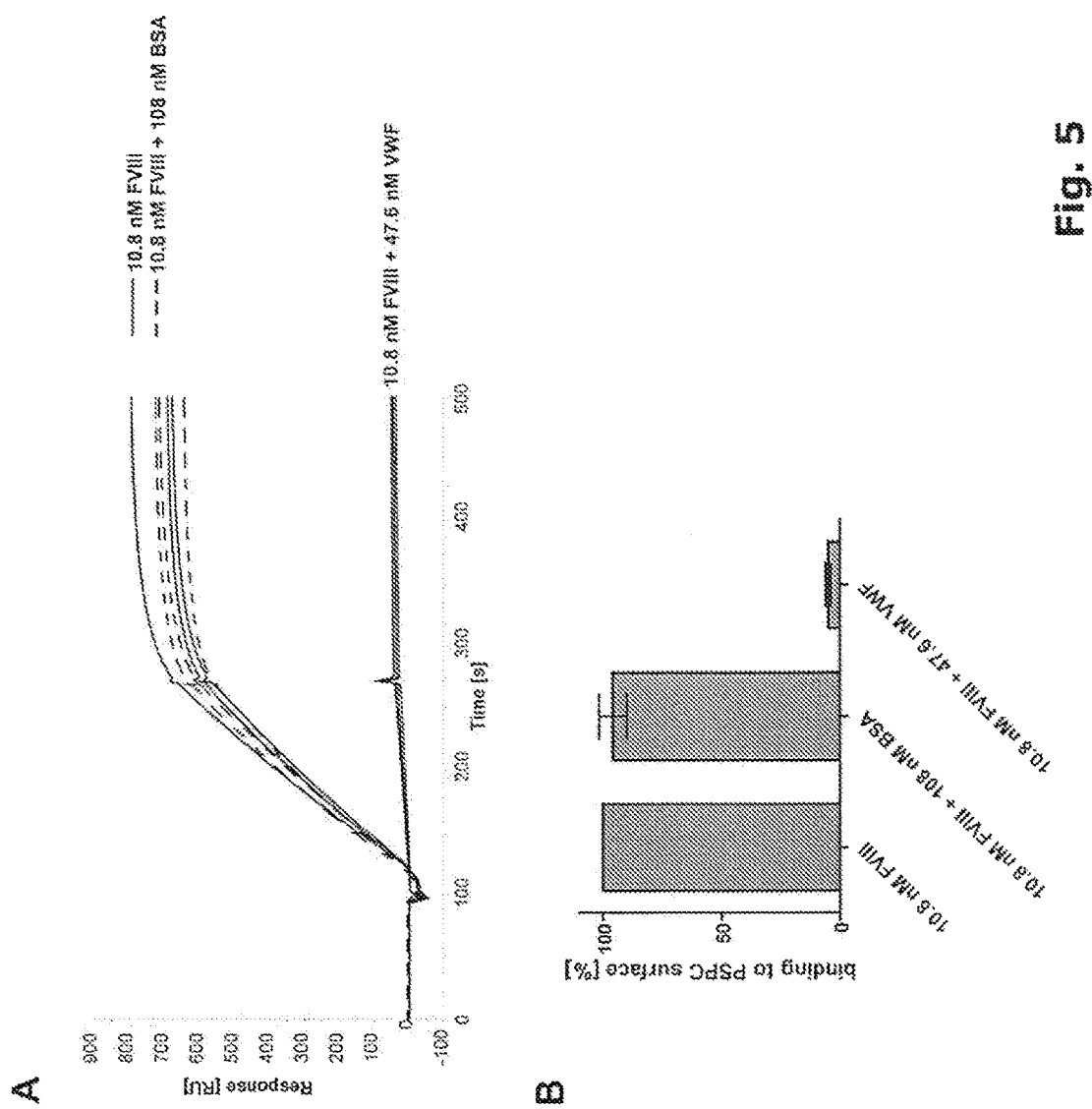
FIG. 5 shows binding of rFVIII to phospholipid monolayer in SPR and inhibition by pdVWF. A-binding sensorgrams of rFVIII and rFVIII in the presence of either 108 nM BSA (bovine serum albumin) or 47.6 nM pdVWF; each sample in triplicate. B—Mean and SD of binding levels measured 120 sec after end of analyte injection expressed as percentage of rFVIII binding; n=3.

Negative controls; Von Willebrand Factor and BSA did not bind to the PSPC surface (not shown), in contrast, a high binding level of rFVIII was shown. This binding could be completely inhibited with Von Willebrand Factor, in contrast addition of high BSA concentration had no effect on the binding (FIG. 5).

Figure 6:
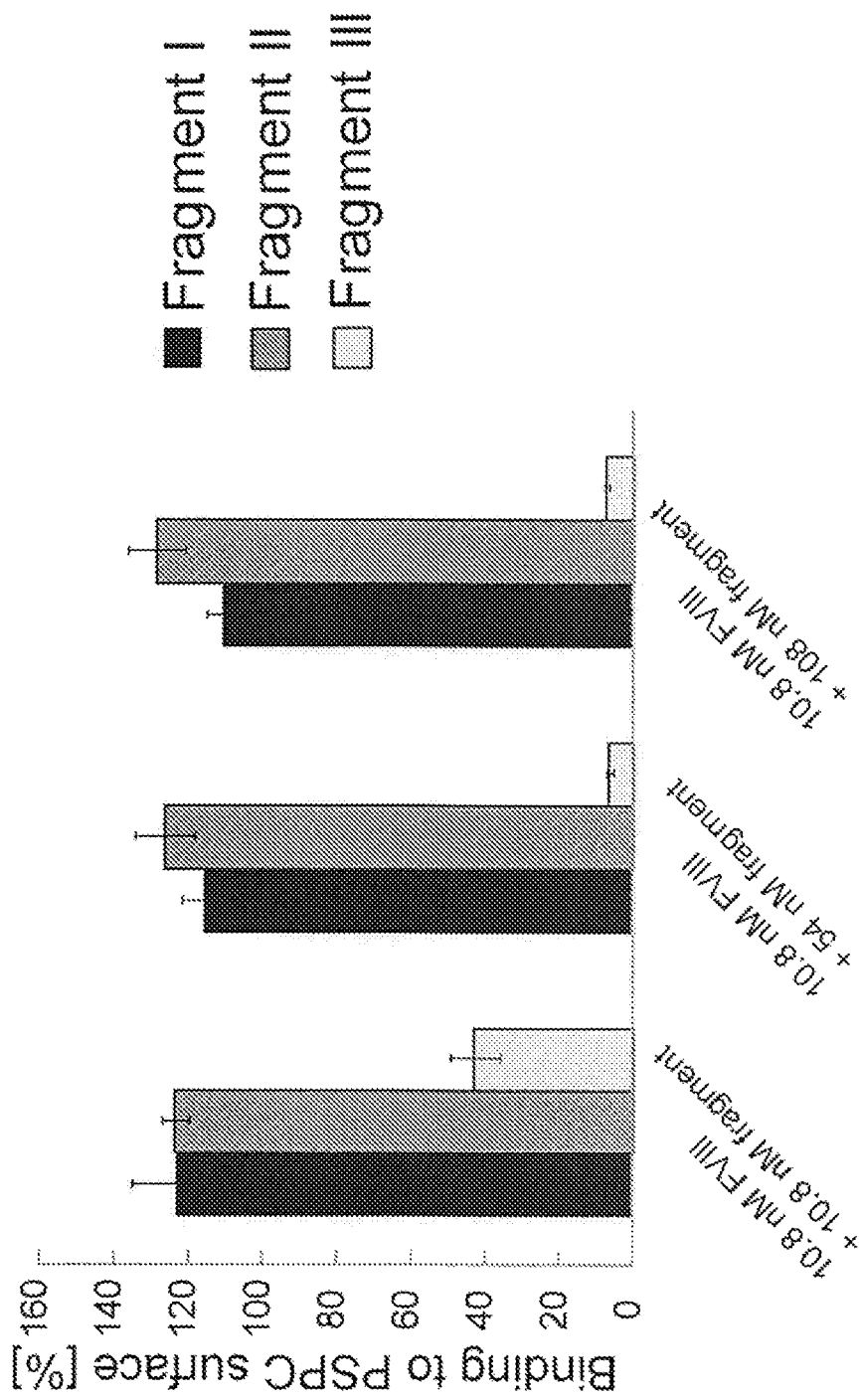
FIG. 6 shows inhibition of the rFVIII-phospholipid interaction by Von Willebrand Factor-derived fragments measured in SPR. rFVIII binding to phospholipid monolayer was performed in the presence of three different concentrations of the three Von Willebrand Factor-derived fragments (concentrations and fragment type are indicated on graph). Graph represents mean and SD of binding levels measured 120 sec after end of analyte injection expressed as percentage of rFVIII binding; n=3.
Figure 7:
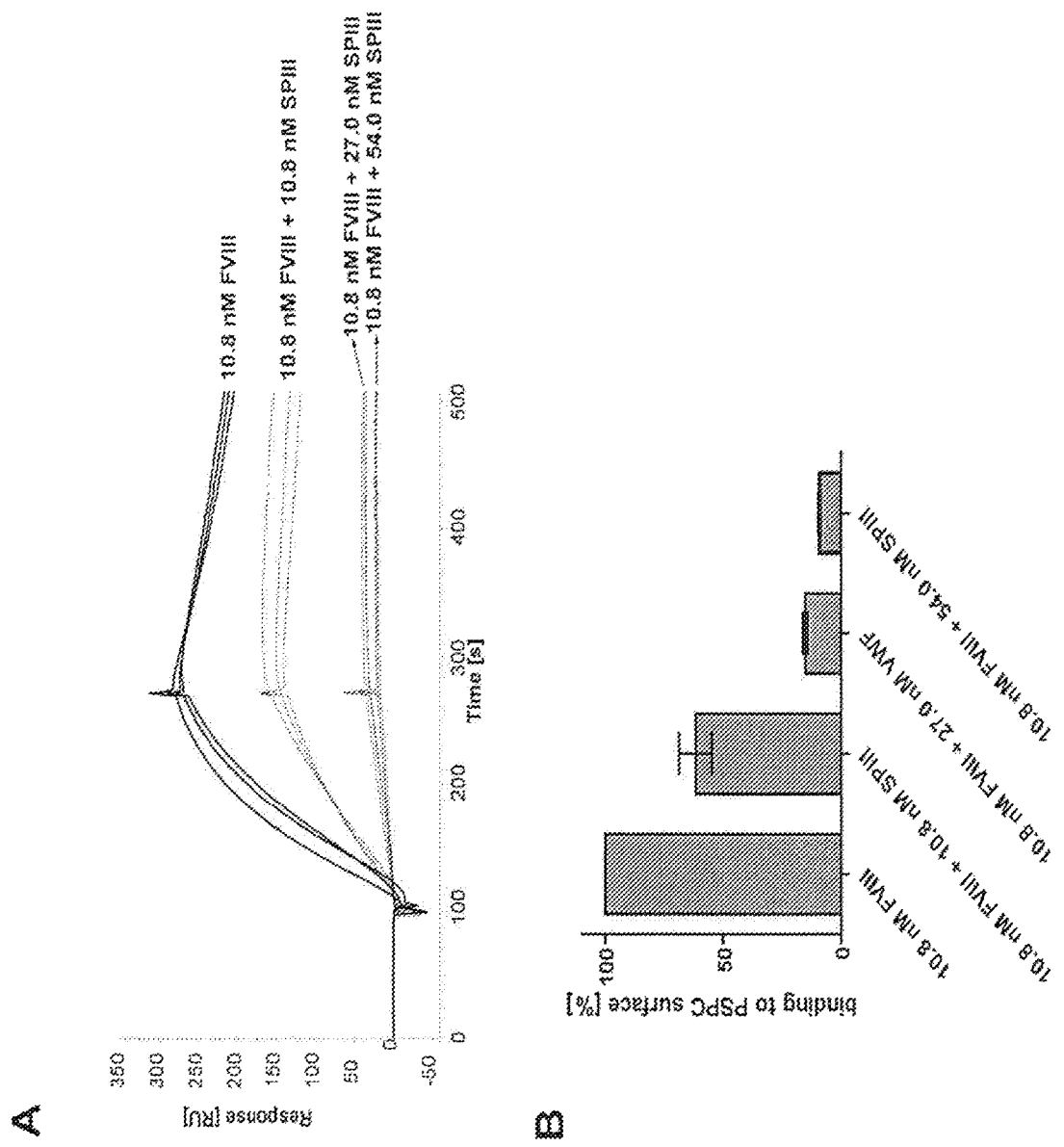
FIG. 7 shows concentration dependent inhibition of rFVIII binding to phospholipid monolayer by fragment III. A-binding sensorgrams of rFVIII to phospholipid monolayer in the presence of different concentrations of the fragment III (concentrations are indicated on graph), each sample in triplicate. B—Mean and SD of binding levels measured 120 sec after end of analyte injection expressed as percentage of rFVIII binding; n=3.

To evaluate, if the fragments obtained by limited digestion were able to inhibit PSPC binding similar to flVWF, the fragments I, II and III were injected over the sensor chip surface. Only fragment III was able to inhibit the interaction between rFVIII and phospholipid monolayer (FIG. 6). This effect was dose dependent with almost complete inhibition at 2.5× excess of fragment III over the rFVIII (FIG. 7).

Example 4

Determination of Collagen III Binding Affinity of flVWF and Fragment III.

Figure 8:
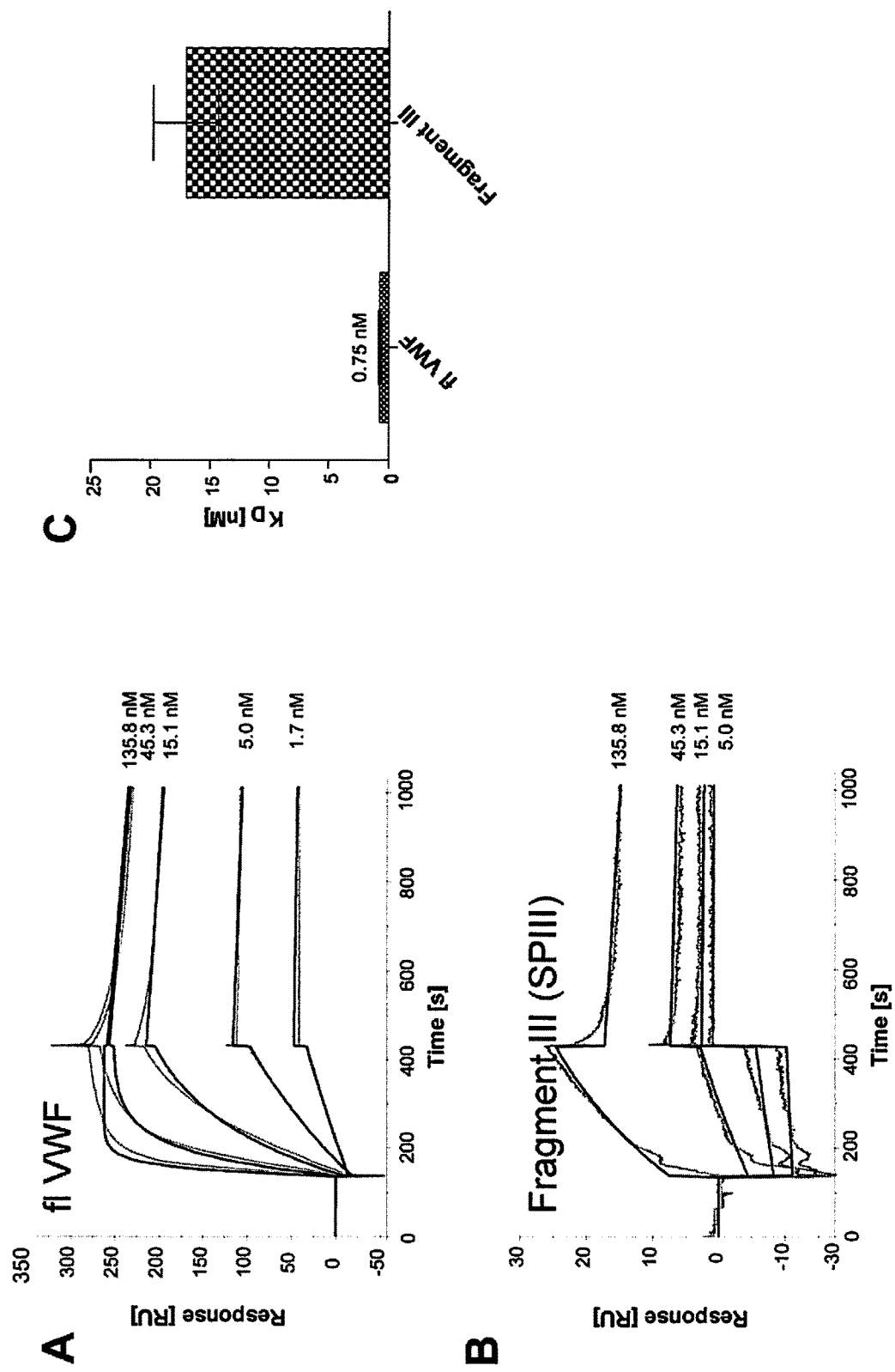
FIG. 8 shows binding of pdVWF and fragment III to collagen type III. A, B—Binding sensorgrams (grey curves), and curve alignment (black curves) representative for the interaction between immobilized collagen type III and pdVWF/purified fragment III. The concentrations and sample type are indicated on the diagram. C—Dissociation constants ($K_D$) expressed as mean and SEM; n=9.

The analysis was carried out using Biacore 2000 instrument (GE Healthcare) according to Romjin et al. 2003 with modifications. Briefly human pepsin-digested collagen type III was covalently bound to the surface of a CM5 sensor chip. Subsequently the samples were injected over the sensor chip surface. The running buffer was 10 mM HEPES, 150 mM NaCl, 3.4 mM EDTA, 0.005% Tween 20. The flVWF bound to collagen III with very high affinity (0.75 nM), the binding of the fragment III was significantly decreased to 17.02 nM (FIG. 8).

Example 5

Determination of Heparin Binding Affinity of flVWF and Fragment III.

Figure 9:
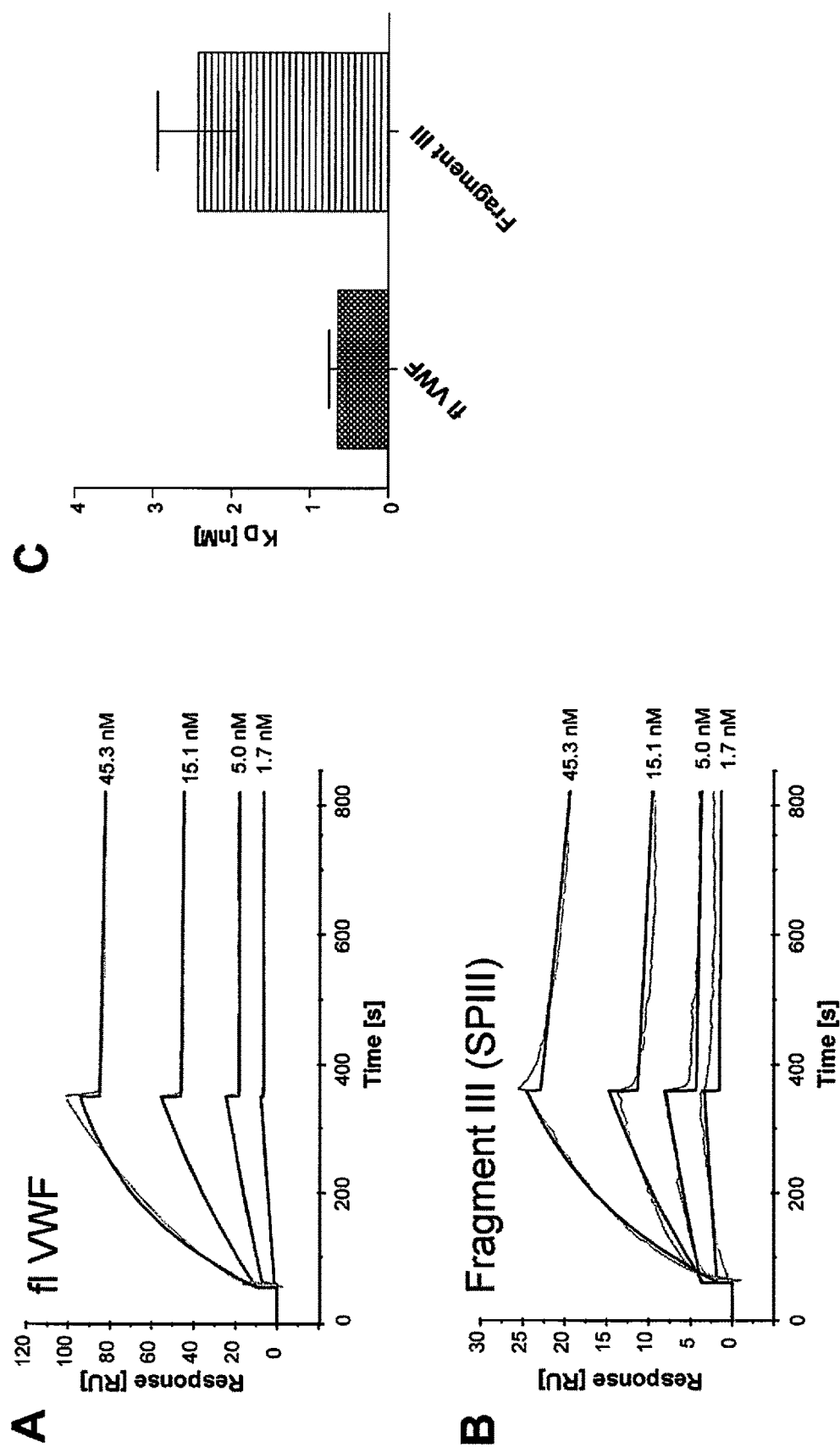
FIG. 9 shows binding of pdVWF and fragment III to heparin. A, B—Binding sensorgrams (grey curves), and curve alignment (black curves) representative for the interaction between immobilized heparin and pdVWF/purified fragment III. The concentrations and sample type are indicated on the diagram. C—Dissociation constants ($K_D$) expressed as mean and SEM; n=6.

The analysis was carried out using Biacore T200 instrument (GE Healthcare) according to Sarafanov et al. 2001. Briefly, heparin from porcine intestinal mucosa was biotinylated using NHS-biotin reagent kit, and bound to the surface of a SA sensor chip. The reference flow cell was coated with biotin. Subsequently the samples were injected over the sensor chip surface. The running buffer was 150 mM HEPES, 150 mM NaCl, 5 mM $CaCl_2$, 0.05 Tween 20. The flVWF bound to heparin with an affinity of 0.65 nM, the binding affinity of the fragment III was significantly decreased to 2.43 nM (FIG. 9).

Example 6

Determination of FVIII or FVIII/VWF Fragment III Complex Recovery and Half Life in Circulation in Haemophilia a Dogs.

Figure 10:
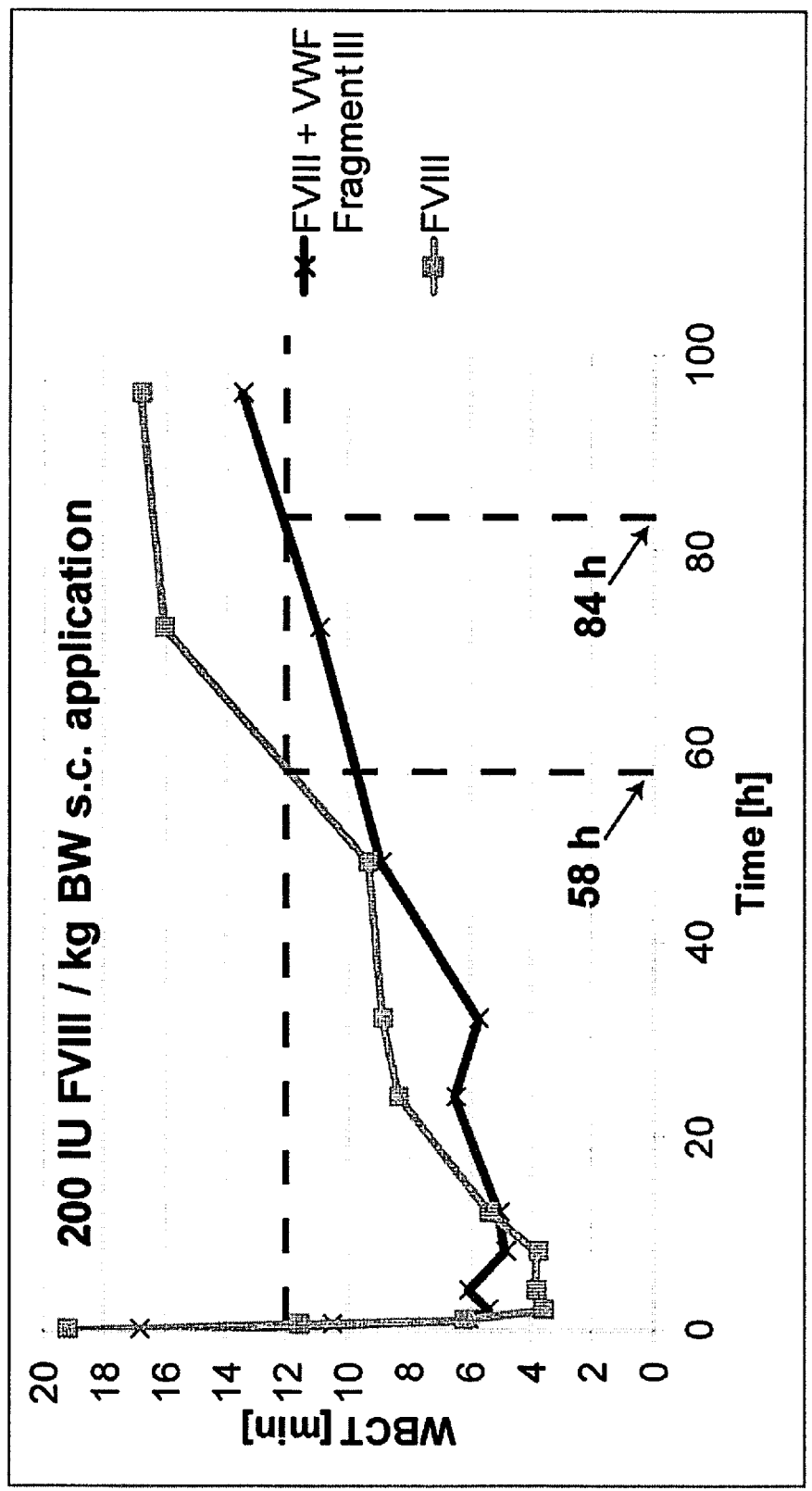
FIG. 10 shows a comparison of whole blood clotting time (WBCT) values measured in blood samples from haemophilia A dogs treated s.c. with FVIII alone or in combination with VWF fragment III. WBCT obtained after s.c. application of FVIII in combination with five-fold molar excess of VWF fragment III applied at 200 IU FVIII/kg BW. Horizontal dashed line marks upper limit of clotting time in normal dogs (12 minutes).
Figure 11:
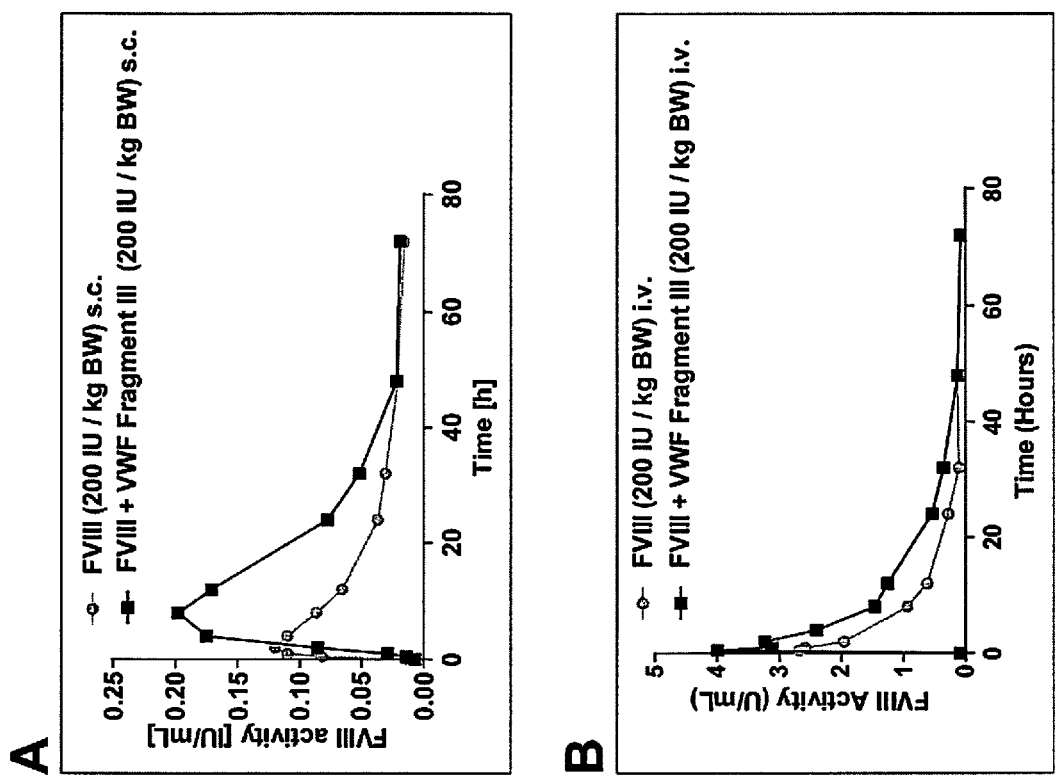
FIG. 11 shows FVIII activity measured with chromogenic FVIII activity assay in haemophilia A dogs plasma samples obtained after application of FVIII or FVIII in combination with VWF fragment III. A—FVIII or FVIII with five fold molar excess of VWF fragment III was applied subcutaneously at 200 IU FVIII/kg BW; the area under the curve (AUC) for the FVIII sample alone was 2.867, and for FVIII in combination with VWF fragment III—4.917. B—FVIII or FVIII with five fold molar excess of VWF fragment III was applied intravenously at 200 IU FVIII/kg BW. The AUC for the FVIII sample alone was 27.69, and for FVIII in combination with VWF fragment III—45.72.

Two haemophilia A dogs were subjected to s.c. and subsequent i.v. injection of recombinant B-domain-deleted FVIII alone or in combination with five-fold molar excess of VWF Fragment III. Dog 1 received 200 IU/kg BW of FVIII alone and Dog 2 received 200 IU/kg BW FVIII in complex with VWF Fragment III. Blood samples were collected at 0.5, 1, 2, 4, 8, 12, 24, 32, 48, 72 and 96 hours after each s.c. or i.v. drug administration. Samples were analyzed for whole blood clotting time (WBCT) and activity in chromogenic FVIII activity assay. The subcutaneous administration of VWF Fragment III in complex with FVIII resulted in 1.4-fold increase in time required to exceed a clotting time for a normal dog comparing with s.c. administration of FVIII alone (FIG. 10). The administration of VWF Fragment III with FVIII resulted also in increased FVIII activity in dog plasma over time and in nearly doubled area under the curve (AUC) values for both, s.c. and i.v. application compared to administration of FVIII alone (FIG. 11).

Example 7

Determination of FVIII Binding Affinity of Recombinant Fragment III Monomer and Dimer.

Figure 12:
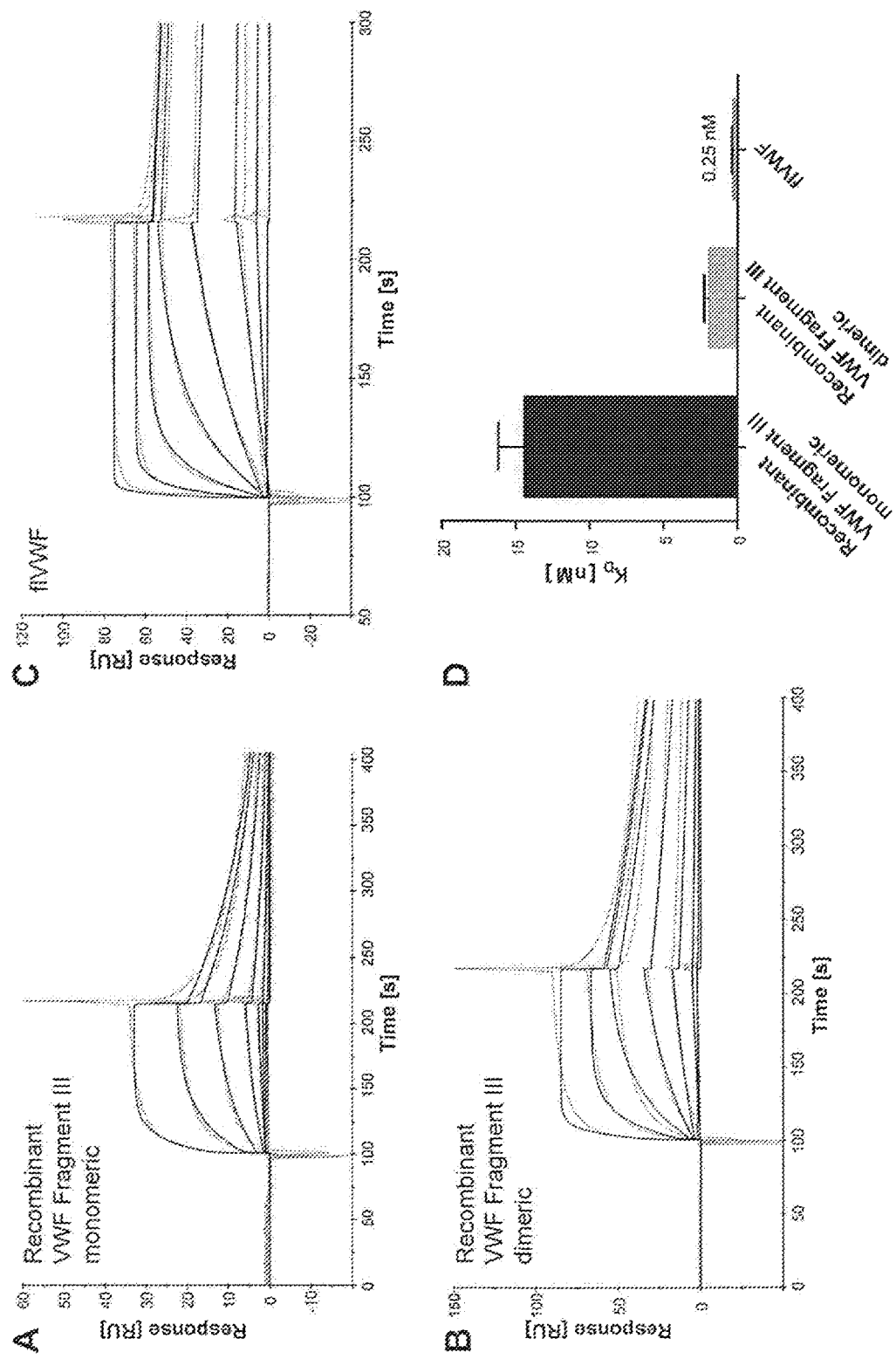
FIG. 12 shows binding of recombinant fragment III monomer, recombinant fragment III dimer and plasma derived VWF (flVWF) to rFVIII. A, B, C-Binding sensorgrams (grey curves), and curve alignment (black curves) representative for the interaction between immobilized VWF or recombinant VWF-fragments and FVIII. The sample type is indicated on the diagram. The concentration of applied FVIII was 0, 0.2, 0.6, 1.7, 5, 15, 45 and 135 nM. D-Dissociation constants ($K_D$) expressed as mean and SD; n=4.

Recombinant fragment III was transiently expressed in HEK293 cell line with a C-terminal Strep-Tag and purified by Strep-tactin affinity chromatography. The fragment III monomers and dimers were separated by size exclusion chromatography (SEC). The analysis was carried out using Biacore 2000 instrument. The fragment III monomers and dimers were immobilized on CM5 and FVIII concentration series was injected over the sensor chip surface. Plasma derived full length VWF was used as control. The running buffer was 150 mM HEPES, 150 mM NaCl, 5 mM $CaCl_2$, 0.05% Tween 20. FVIII bound to fragment III dimer with an affinity constant of 1.9 nM. The affinity of FVIII to the monomeric Fragment III was significantly lower ($K_D$=14.3 nM) (FIG. 12).

Example 8

Stabilisation of rFVIII in Solution by VWF Fragment III.

Figure 13:
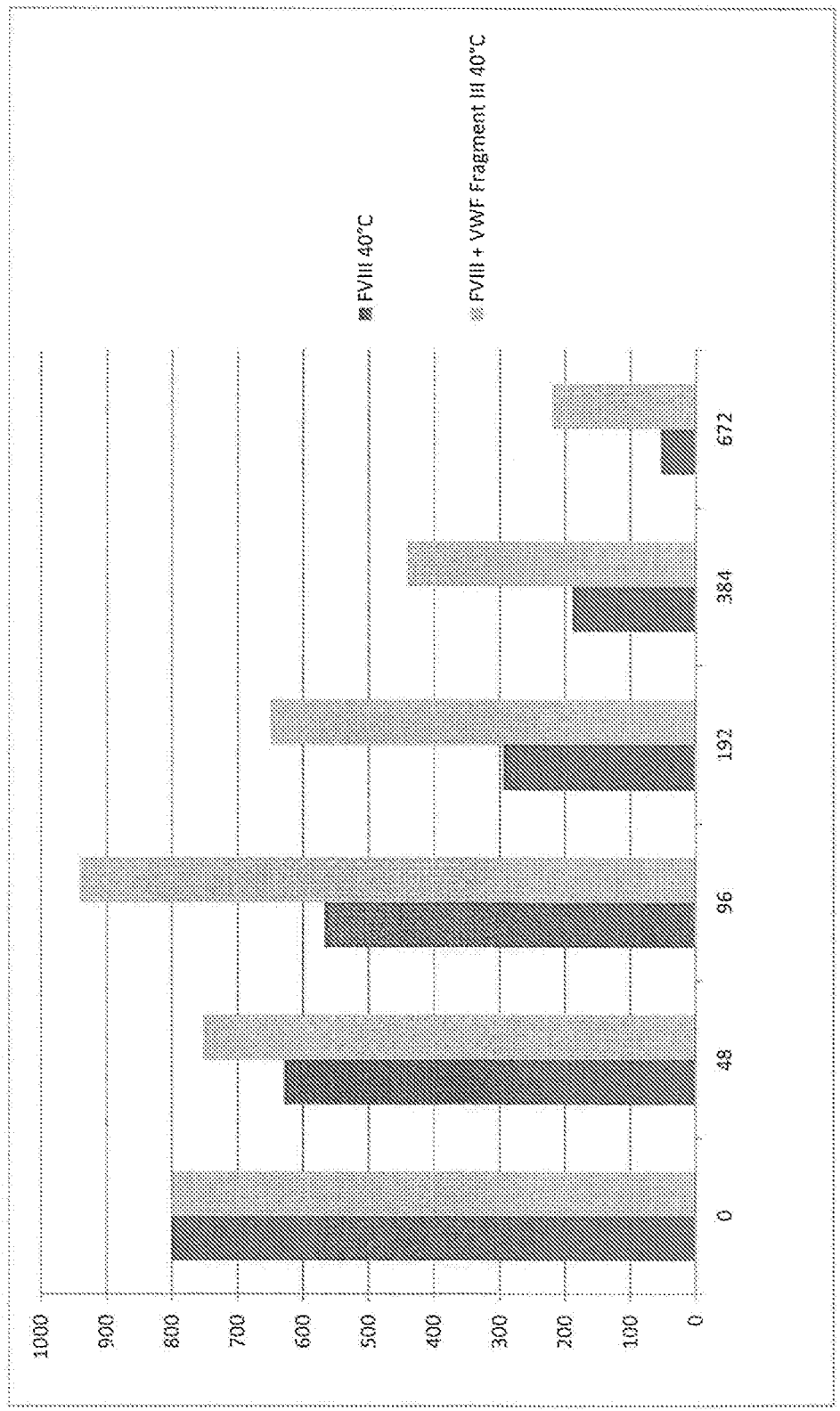
FIG. 13 shows stabilisation of FVIII by VWF fragment III. FVIII activity of FVIII alone or FVIII in complex with VWF fragment III incubated at 40° C. measured at different time points.

2000 IU of recombinant FVIII (Nuwiq®) was reconstituted in 2.5 ml water, with or without addition of five-fold molar excess VWF Fragment III. Both preparations were incubated at 40° C. and aliquots were taken at 48, 96, 192, 384, 408 and 672 hours. Samples were analysed for FVIII activity in a chromogenic FVIII activity assay. VWF Fragment III contributed to significant longer activity of FVIII at 40° C. (FIG. 13).

Example 9

Comparison of Heparin Binding Between Recombinant Fragment III and NovoSeq21 Fragment.

Figure 14:
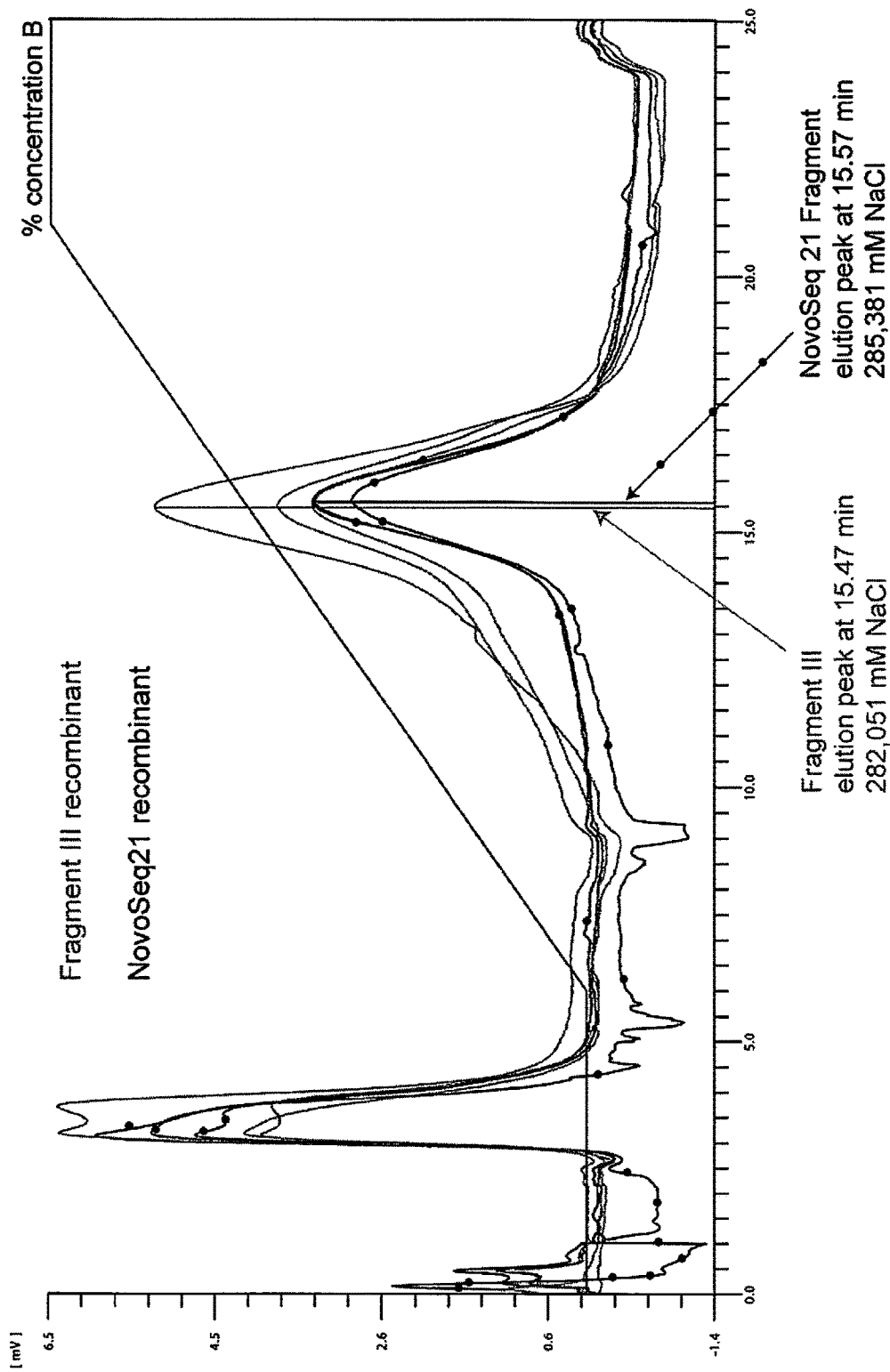
FIG. 14 shows Heparin binding using heparin affinity chromatography of two VWF fragments as described in Example 9.

Recombinant fragment III and NovoSeq21 (SEQ ID No 21 from WO2013/160005A1) fragment were transiently expressed in HEK293 cell line with a C-terminal Strep-Tag and purified by Strep-tactin affinity chromatography. Heparin binding was tested using heparin affinity chromatography. Both recombinant fragments were bound to heparin column (HiTrap Heparin HP 1 ml, GE Healthcare) and eluted with linear salt gradient ranging from 0-500 mM NaCl. Both fragments were run in triplicates, see FIG. 14. The mean elution peak for the NovoSeq21 fragment was at 15.57±0.04 min which corresponds to 285.381 mM NaCl, and for the fragment III at 15.47±0.02 min which corresponds to 282.051 mM NaCl. This indicates higher heparin affinity for the NovoSeq21 fragment.

Analytical Methods

Description of Analytical Methods

FVIII: C, Screening Method Based on Coatest

The method is based on the two-stage principle, and was performed using micro plate technique. In stage one, activated factor X (Xa) is generated via the intrinsic pathway where FVIII: C acts as a co-factor. In stage two, Factor Xa is then determined by the use of a synthetic chromogenic substrate, S-2222 in the presence of a thrombin inhibitor 1-2581 to prevent hydrolysis of the substrate by thrombin. The reaction is stopped with acid, and the VIII: C activity, which is proportional to the release of pNA (para-nitroaniline), is determined photo metrically at 405 nm against a reagent blank.

The method complies with the requirements in the European Pharmacopoeia. The unit of FVIII: C is expressed in international units (IU) as defined in the current International Concentrate Standard (IS) established by the World Health Organization (WHO). The routine using buffer containing 1% BSA instead of severe hemophilic plasma for predilutions has been validated. See also literature references (European Pharmacopoeia Supplement 2000, general Methods, 2.7.4. Assay of Blood Coagulation FVIII; Rosen S (1984) Assay of FVIII: C with a Chromogenic Substrate. 3, Haematol, Suppl 40, vol 33, 139-145, 1984; Carlebjörk G, Oswaldsson U, Rosen S (1987) A simple and accurate micro plate assay for the determination of FVIII activity. Thrombosis Research 47; 5-14, 1987; Mire-Sluis A R, Gerrard T, Gaines das R, Padilla A and Thorpe R. Biological assays: Their Role in the development and quality Control of Recombinant Biological Medicinal Products. Biological, 24, 351-362 (1996)).

Determination of Total Protein According to Bradford

Protein determination according to Bradford is based on the observation that the absorbance maximum for an acidic solution of Coomassie Brilliant Blue G-250 shifts from 465 nm to 595 nm when binding to protein occurs. Both hydrophobic and ionic interactions stabilize the anionic form of the dye, causing a visible colour change. The assay is useful since the extinction coefficient of a dye-albumin complex solution is constant over a 10-fold concentration range. See also reference Bradford, M M. A rapid and sensitive method for the quantisation of microgram quantities of protein utilizing the principle of protein-dye binding. *Analytical Biochemistry* 72: 248-254. 1976. for further information.

Determination of Total Protein According to Amino Acid Analysis (AAA)

Before the AAA all proteins are hydrolyzed by 6 M HCl for 24 h at 110° C. The amino acids are separated by cation-exchange chromatography on sulphonated polystyrene resins and detected continuously in the eluent. The detection is based on post-column ninhydrin derivatisation using a dual photometer for simultaneous measurement at 440 nm for proline and hydroxyproline and 570 nm for all other amino acids. The amino acids asparagine and glutamine are both deamidated during MA and are determined as aspartic acid and glutamic acid, respectively. Thus, the results of aspartic acid and glutamic acid represent the sum of aspartic acid/asparagine (Asx) and glutamic acid/glutamine (Glx), respectively, in the original sample. Tryptophan is not generating a distinct response using this method, and, thus, is not quantified by the MA. Cysteine is destroyed during the hydrolysis and is not quantified. The AAA is further described in reference: Total protein MA analytical method. Spackman, D. H., Stein, W. H., and Moore, S. (1958) Anal. Biochem. 30: 1190-1206.

Purity or specific activity (FVIII:C/Total protein)

The purity (or also called specific activity) for a sample, is calculated taking the value achieved from the FVIII:C analysis and divide it with the value achieved from the analysis of total protein.

SDS-PAGE (Molecular Weight Distribution)

SDS polyacrylamide gel electrophoresis (SDS-PAGE) involves the separation of proteins based on their size. This method describes the SDS-PAGE of proteins, which is run under reduced conditions. By heating the sample under denaturing and reducing conditions, proteins become unfolded and coated with anionic detergent sodium dodecyl sulphate (SDS), acquiring a high net negative charge that is proportional to the length of the polypeptide chain. When loaded onto a polyacrylamide gel matrix and placed in an electric field, the negatively charged protein molecules migrate towards the positively charged electrode and are separated by a molecular sieving effect, i.e. by their molecular weight. Polyacrylamide gels restrain larger molecules from migrating as fast as smaller molecules. Because the charge-to-mass ratio is nearly the same among SDS-denatured polypeptides, the final separation of proteins is dependent almost entirely on the differences in relative molecular mass of polypeptides. In a gel of uniform density the relative migration distance of a protein ($R_f$) is negatively proportional to the log of its mass. If proteins of known mass are run simultaneously with the unknowns, the relationship between Rf and mass can be plotted, and the masses of unknown proteins estimated. The protein bands separated by electrophoresis are visualized by silver staining. Evaluation is done visually by judging the appearances of the standards, reference (control sample) and analysed samples.

Factor VIII Antigen Content (FVIII:Ag)

The amount of Factor VIII antigen content (FVIII:Ag) is measured with a ELISA kit (ASSERACHROM® VIII:Ag, enzyme immunoassay for Factor VIII, kit, Diagnostica Stago (France), as further described[18] with replacement of the provided kit buffer with Tris-NaCl buffer+1% bovine serum albumin for sample dilutions.

Size Exclusion Chromatography (SEC)

Monomer, aggregate and fragment is measured using a size exclusion chromatography (SEC-HPLC) analytical column (Superdex 200, 10/300 GL, GE Healthcare) processed under native buffer conditions (25 mM HEPES, 0.5M NaCl, 0.3M arginine, 50 mM $CaCl_2$, 0.02% Polysorbate 80, pH 7.5). Sample load is approximately 1% of the size exclusion column and the Factor VIII:C concentration is approximately 1000 IU/ml.

Western Blot Against Factor VIII

Factor VIII degeneration product based on size is measured using FVIII Western Blot. FVIII molecular mass distribution proteins and peptides in factor VIII preparations are separated according to molecular mass by sodium dodecyl sulphate (SDS) polyacrylamide gel electrophoresis (PAGE) under reducing conditions. Thereafter, the proteins are transferred electrophoretically from the gel matrix to a nitrocellulose membrane which is subsequently incubated with a blocking agent. Commercial available polyclonal sheep antibodies directed to the whole human factor VIII molecule is then added followed by a secondary enzyme-labelled antibody as a probe. As a third step a chemiluminescent substrate is added and when combined with the enzyme, light is produced as a by-product. The light output is captured as a real time image using a cooled Charge-Coupled Device camera. The intensity of the signal is correlated with the abundance of the antigen (FVIII) on the blotting membrane.

2D-PAGE

2D-Electrophoresis with Silver Staining was carried out in order to study the electrophoretic band pattern of the Factor VIII protein chain. Isoelectric focusing was performed as the first dimension run using a linear pH gradient of pH 3 to 10. The second dimension SDS-PAGE was run using Tris-Acetate (3-8%) gels. The gels were stained with silver-stain following the second dimension run.

Total Protein (Bradford)

Protein determination according to Bradford is based on the observation that the absorbance maximum for an acidic solution of Coomassie Brilliant Blue G-250 shifts from 465 nm to 595 nm when binding to protein occurs. Both hydrophobic and ionic interactions stabilize the anionic form of the dye, causing a visible colour change. The assay is useful since the extinction coefficient of a dye-albumin complex solution is constant over a 10-fold concentration range. See also reference Bradford, M M. A rapid and sensitive method for the quantisation of microgram quantities of protein utilizing the principle of protein-dye binding. *Analytical Biochemistry* 72: 248-254. 1976. for further information.

All references cited herein are incorporated by reference to the full extent to which the incorporation is not inconsistent with the express teachings herein.

The invention claimed is:

1. A composition comprising a complex of Factor VIII and one or more Von Willebrand Factor peptides, wherein the Von Willebrand Factor peptides comprise at least the amino acids 764 to 1035 and 1691 to 1905 of SEQ ID No. 1 but not amino acids 2255 to 2645 of SEQ ID No. 1.

2. The composition of claim 1, wherein the Von Willebrand Factor peptides are fragments of Von Willebrand factor.

3. The composition of claim 2, wherein the fragments of Von Willebrand Factor comprise amino acids 764 to 1905 of SEQ ID No. 1.

4. The composition of claim 2, wherein the fragments of Von Willebrand factor have an amino acid sequence that corresponds to the amino acid sequence of SEQ ID No. 1 starting from amino acid 764 and ending between amino acid 1905 and 2153 with up to 10 deletions, insertions or substitutions.

5. The composition according to claim 1 wherein the Von Willebrand Factor peptide has a molecular weight of <500 kD.

6. The composition of claim 1, wherein the Von Willebrand Factor peptides have at least one property selected from the group consisting of
 (i) an affinity binding constant for heparin of $K_D>1$ nM;
 (ii) an affinity binding constant for collagen III of $K_D>5$ nM;
 (iii) an affinity binding constant for Factor VIII of $K_D<100$ nM; and
 (iv) an inhibition of Factor VIII phospholipid binding of at least 70%.

7. A composition according to claim 1, wherein the Von Willebrand Factor peptides are derived from Willebrand Factor by proteolytic cleavage or chemical cleavage.

8. The composition of claim 1, wherein Factor VIII is a full length Factor VIII, a B-domain deleted Factor VIII or a Factor VIII with a different size of the B-domain.

9. The composition of claim 1, wherein Factor VIII is plasma derived Factor VIII or recombinant Factor VIII.

10. The composition of claim 1, wherein the composition has at least one of the properties selected from the group consisting of
 (i) the Von Willebrand Factor peptides shield Factor VIII from antibody binding to minimize inhibitor formation in a patient;
 (ii) stabilises Factor VIII to provide a remaining Factor VIII activity of at least 90% after storage for 12 month in a frozen liquid form at −70° C.;
 (iii) stabilises Factor VIII to provide a remaining Factor VIII activity of at least 90% after storage for 24 month in a freeze-dried form at 5° C.;
 (iv) stabilises Factor VIII to provide a remaining Factor VIII activity of at least 90% after storage for 12 month in a freeze-dried form at 25° C.;
 (v) prolongs half-life of Factor VIII in-vivo by at least 20%; and
 (vi) reduces inhibitor formation in previously untreated patients to less than 20% after treatment with the composition for 6 months.

11. A method of using the composition of claim 1 comprising administering the composition to a patient for treatment or prevention of a bleeding disorder.

12. The method according to claim 11, comprising non-intravenous administration of the composition.

13. A method for virus reduction in a preparation of claim 1 comprising the step of nanofiltrating the Von Willebrand Factor peptides prior or after a combination with Factor VIII, whereby porcine parvovirus, if present, is reduced by at least a factor of 100.

14. A method of preparing Von Willebrand Factor peptides comprising the following steps:
 incubating Von Willebrand Factor with *S. aureus* V-8 protease for 2 to 16 hours at an enzyme to Von Willebrand Factor weight/weight ratio of 1:5 to 1:100
 binding and purifying on an anion exchanger and collecting the desired purified vWF peptides in a fraction coming from the anion exchanger by applying an increased amount of salt concentration.

15. The composition according to claim 1 wherein the Von Willebrand Factor peptide has a molecular weight of <400 kD.

16. The composition of claim 1, wherein the Von Willebrand Factor peptides have at least one property selected from the group consisting of
 (i) an affinity binding constant for heparin of $K_D \geq 2.43$ nM;
 (ii) an affinity binding constant for collagen III of $K_D \leq 17.02$ nM;
 (iii) an affinity binding constant for Factor VIII of $K_D \leq 6.19$ nM; and
 (iv) an inhibition of Factor VIII phospholipid binding of at least 80%.

17. A composition according to claim 1, wherein the Von Willebrand Factor peptides are derived from Willebrand Factor by proteolytic cleavage with *S. aureus*.

18. The composition of claim 1, wherein Factor VIII is plasma derived Factor VIII or recombinant Factor VIII, wherein the recombinant Factor VIII is expressed in a human cell line.

19. The method according to claim 11, comprising administration of the composition by subcutaneous injection.

* * * * *

SEQUENCE LISTING

```
<160> NUMBER OF SEQ ID NOS: 7

<210> SEQ ID NO 1
<211> LENGTH: 2813
<212> TYPE: PRT
<213> ORGANISM: Homo sapiens

<400> SEQUENCE: 1

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
                20                  25                  30

Ala Arg Cys Ser Leu Phe Gly Ser Asp Phe Val Asn Thr Phe Asp Gly
            35                  40                  45

Ser Met Tyr Ser Phe Ala Gly Tyr Cys Ser Tyr Leu Leu Ala Gly Gly
        50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
                100                 105                 110

Tyr Ala Ser Lys Gly Leu Tyr Leu Glu Thr Glu Ala Gly Tyr Tyr Lys
            115                 120                 125

Leu Ser Gly Glu Ala Tyr Gly Phe Val Ala Arg Ile Asp Gly Ser Gly
        130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
                180                 185                 190

Leu Ser Ser Gly Glu Gln Trp Cys Glu Arg Ala Ser Pro Pro Ser Ser
            195                 200                 205

Ser Cys Asn Ile Ser Ser Gly Glu Met Gln Lys Gly Leu Trp Glu Gln
        210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
                260                 265                 270

Arg Thr Cys Ala Gln Glu Gly Met Val Leu Tyr Gly Trp Thr Asp His
            275                 280                 285

Ser Ala Cys Ser Pro Val Cys Pro Ala Gly Met Glu Tyr Arg Gln Cys
        290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
```

```
                    325                 330                 335
Leu Asp Glu Gly Leu Cys Val Glu Ser Thr Glu Cys Pro Cys Val His
                340                 345                 350

Ser Gly Lys Arg Tyr Pro Pro Gly Thr Ser Leu Ser Arg Asp Cys Asn
            355                 360                 365

Thr Cys Ile Cys Arg Asn Ser Gln Trp Ile Cys Ser Asn Glu Glu Cys
        370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
    610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
    690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750
```

```
Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
        770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
        820                 825                 830

Gly Lys Glu Tyr Ala Pro Gly Glu Thr Val Lys Ile Gly Cys Asn Thr
        835                 840                 845

Cys Val Cys Gln Asp Arg Lys Trp Asn Cys Thr Asp His Val Cys Asp
        850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
                900                 905                 910

Gly Cys Ser His Pro Ser Val Lys Cys Lys Lys Arg Val Thr Ile Leu
        915                 920                 925

Val Glu Gly Gly Glu Ile Glu Leu Phe Asp Gly Glu Val Asn Val Lys
        930                 935                 940

Arg Pro Met Lys Asp Glu Thr His Phe Glu Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
        980                 985                 990

Cys Gly Leu Cys Gly Asn Phe Asp Gly Ile Gln Asn Asn Asp Leu Thr
        995                 1000                1005

Ser Ser Asn Leu Gln Val Glu Glu Asp Pro Val Asp Phe Gly Asn
        1010                1015                1020

Ser Trp Lys Val Ser Ser Gln Cys Ala Asp Thr Arg Lys Val Pro
        1025                1030                1035

Leu Asp Ser Ser Pro Ala Thr Cys His Asn Asn Ile Met Lys Gln
        1040                1045                1050

Thr Met Val Asp Ser Ser Cys Arg Ile Leu Thr Ser Asp Val Phe
        1055                1060                1065

Gln Asp Cys Asn Lys Leu Val Asp Pro Glu Pro Tyr Leu Asp Val
        1070                1075                1080

Cys Ile Tyr Asp Thr Cys Ser Cys Glu Ser Ile Gly Asp Cys Ala
        1085                1090                1095

Cys Phe Cys Asp Thr Ile Ala Ala Tyr Ala His Val Cys Ala Gln
        1100                1105                1110

His Gly Lys Val Val Thr Trp Arg Thr Ala Thr Leu Cys Pro Gln
        1115                1120                1125

Ser Cys Glu Glu Arg Asn Leu Arg Glu Asn Gly Tyr Glu Cys Glu
        1130                1135                1140

Trp Arg Tyr Asn Ser Cys Ala Pro Ala Cys Gln Val Thr Cys Gln
        1145                1150                1155
```

-continued

```
His Pro Glu Pro Leu Ala Cys Pro Val Gln Cys Val Glu Gly Cys
1160                1165                1170

His Ala His Cys Pro Pro Gly Lys Ile Leu Asp Glu Leu Leu Gln
1175                1180                1185

Thr Cys Val Asp Pro Glu Asp Cys Pro Val Cys Glu Val Ala Gly
1190                1195                1200

Arg Arg Phe Ala Ser Gly Lys Lys Val Thr Leu Asn Pro Ser Asp
1205                1210                1215

Pro Glu His Cys Gln Ile Cys His Cys Asp Val Val Asn Leu Thr
1220                1225                1230

Cys Glu Ala Cys Gln Glu Pro Gly Gly Leu Val Val Pro Pro Thr
1235                1240                1245

Asp Ala Pro Val Ser Pro Thr Thr Leu Tyr Val Glu Asp Ile Ser
1250                1255                1260

Glu Pro Pro Leu His Asp Phe Tyr Cys Ser Arg Leu Leu Asp Leu
1265                1270                1275

Val Phe Leu Leu Asp Gly Ser Ser Arg Leu Ser Glu Ala Glu Phe
1280                1285                1290

Glu Val Leu Lys Ala Phe Val Val Asp Met Met Glu Arg Leu Arg
1295                1300                1305

Ile Ser Gln Lys Trp Val Arg Val Ala Val Val Glu Tyr His Asp
1310                1315                1320

Gly Ser His Ala Tyr Ile Gly Leu Lys Asp Arg Lys Arg Pro Ser
1325                1330                1335

Glu Leu Arg Arg Ile Ala Ser Gln Val Lys Tyr Ala Gly Ser Gln
1340                1345                1350

Val Ala Ser Thr Ser Glu Val Leu Lys Tyr Thr Leu Phe Gln Ile
1355                1360                1365

Phe Ser Lys Ile Asp Arg Pro Glu Ala Ser Arg Ile Thr Leu Leu
1370                1375                1380

Leu Met Ala Ser Gln Glu Pro Gln Arg Met Ser Arg Asn Phe Val
1385                1390                1395

Arg Tyr Val Gln Gly Leu Lys Lys Lys Lys Val Ile Val Ile Pro
1400                1405                1410

Val Gly Ile Gly Pro His Ala Asn Leu Lys Gln Ile Arg Leu Ile
1415                1420                1425

Glu Lys Gln Ala Pro Glu Asn Lys Ala Phe Val Leu Ser Ser Val
1430                1435                1440

Asp Glu Leu Glu Gln Gln Arg Asp Glu Ile Val Ser Tyr Leu Cys
1445                1450                1455

Asp Leu Ala Pro Glu Ala Pro Pro Pro Thr Leu Pro Pro Asp Met
1460                1465                1470

Ala Gln Val Thr Val Gly Pro Gly Leu Leu Gly Val Ser Thr Leu
1475                1480                1485

Gly Pro Lys Arg Asn Ser Met Val Leu Asp Val Ala Phe Val Leu
1490                1495                1500

Glu Gly Ser Asp Lys Ile Gly Glu Ala Asp Phe Asn Arg Ser Lys
1505                1510                1515

Glu Phe Met Glu Glu Val Ile Gln Arg Met Asp Val Gly Gln Asp
1520                1525                1530

Ser Ile His Val Thr Val Leu Gln Tyr Ser Tyr Met Val Thr Val
1535                1540                1545

Glu Tyr Pro Phe Ser Glu Ala Gln Ser Lys Gly Asp Ile Leu Gln
```

-continued

```
            1550                1555                1560
Arg Val Arg Glu Ile Arg Tyr Gln Gly Gly Asn Arg Thr Asn Thr
    1565                1570                1575
Gly Leu Ala Leu Arg Tyr Leu Ser Asp His Ser Phe Leu Val Ser
    1580                1585                1590
Gln Gly Asp Arg Glu Gln Ala Pro Asn Leu Val Tyr Met Val Thr
    1595                1600                1605
Gly Asn Pro Ala Ser Asp Glu Ile Lys Arg Leu Pro Gly Asp Ile
    1610                1615                1620
Gln Val Val Pro Ile Gly Val Gly Pro Asn Ala Asn Val Gln Glu
    1625                1630                1635
Leu Glu Arg Ile Gly Trp Pro Asn Ala Pro Ile Leu Ile Gln Asp
    1640                1645                1650
Phe Glu Thr Leu Pro Arg Glu Ala Pro Asp Leu Val Leu Gln Arg
    1655                1660                1665
Cys Cys Ser Gly Glu Gly Leu Gln Ile Pro Thr Leu Ser Pro Ala
    1670                1675                1680
Pro Asp Cys Ser Gln Pro Leu Asp Val Ile Leu Leu Leu Asp Gly
    1685                1690                1695
Ser Ser Ser Phe Pro Ala Ser Tyr Phe Asp Glu Met Lys Ser Phe
    1700                1705                1710
Ala Lys Ala Phe Ile Ser Lys Ala Asn Ile Gly Pro Arg Leu Thr
    1715                1720                1725
Gln Val Ser Val Leu Gln Tyr Gly Ser Ile Thr Thr Ile Asp Val
    1730                1735                1740
Pro Trp Asn Val Val Pro Glu Lys Ala His Leu Leu Ser Leu Val
    1745                1750                1755
Asp Val Met Gln Arg Glu Gly Gly Pro Ser Gln Ile Gly Asp Ala
    1760                1765                1770
Leu Gly Phe Ala Val Arg Tyr Leu Thr Ser Glu Met His Gly Ala
    1775                1780                1785
Arg Pro Gly Ala Ser Lys Ala Val Val Ile Leu Val Thr Asp Val
    1790                1795                1800
Ser Val Asp Ser Val Asp Ala Ala Asp Ala Ala Arg Ser Asn
    1805                1810                1815
Arg Val Thr Val Phe Pro Ile Gly Ile Gly Asp Arg Tyr Asp Ala
    1820                1825                1830
Ala Gln Leu Arg Ile Leu Ala Gly Pro Ala Gly Asp Ser Asn Val
    1835                1840                1845
Val Lys Leu Gln Arg Ile Glu Asp Leu Pro Thr Met Val Thr Leu
    1850                1855                1860
Gly Asn Ser Phe Leu His Lys Leu Cys Ser Gly Phe Val Arg Ile
    1865                1870                1875
Cys Met Asp Glu Asp Gly Asn Glu Lys Arg Pro Gly Asp Val Trp
    1880                1885                1890
Thr Leu Pro Asp Gln Cys His Thr Val Thr Cys Gln Pro Asp Gly
    1895                1900                1905
Gln Thr Leu Leu Lys Ser His Arg Val Asn Cys Asp Arg Gly Leu
    1910                1915                1920
Arg Pro Ser Cys Pro Asn Ser Gln Ser Pro Val Lys Val Glu Glu
    1925                1930                1935
Thr Cys Gly Cys Arg Trp Thr Cys Pro Cys Val Cys Thr Gly Ser
    1940                1945                1950
```

-continued

```
Ser Thr Arg His Ile Val Thr Phe Asp Gly Gln Asn Phe Lys Leu
    1955                1960                1965

Thr Gly Ser Cys Ser Tyr Val Leu Phe Gln Asn Lys Glu Gln Asp
    1970                1975                1980

Leu Glu Val Ile Leu His Asn Gly Ala Cys Ser Pro Gly Ala Arg
    1985                1990                1995

Gln Gly Cys Met Lys Ser Ile Glu Val Lys His Ser Ala Leu Ser
    2000                2005                2010

Val Glu Leu His Ser Asp Met Glu Val Thr Val Asn Gly Arg Leu
    2015                2020                2025

Val Ser Val Pro Tyr Val Gly Gly Asn Met Glu Val Asn Val Tyr
    2030                2035                2040

Gly Ala Ile Met His Glu Val Arg Phe Asn His Leu Gly His Ile
    2045                2050                2055

Phe Thr Phe Thr Pro Gln Asn Asn Glu Phe Gln Leu Gln Leu Ser
    2060                2065                2070

Pro Lys Thr Phe Ala Ser Lys Thr Tyr Gly Leu Cys Gly Ile Cys
    2075                2080                2085

Asp Glu Asn Gly Ala Asn Asp Phe Met Leu Arg Asp Gly Thr Val
    2090                2095                2100

Thr Thr Asp Trp Lys Thr Leu Val Gln Glu Trp Thr Val Gln Arg
    2105                2110                2115

Pro Gly Gln Thr Cys Gln Pro Ile Leu Glu Glu Gln Cys Leu Val
    2120                2125                2130

Pro Asp Ser Ser His Cys Gln Val Leu Leu Leu Pro Leu Phe Ala
    2135                2140                2145

Glu Cys His Lys Val Leu Ala Pro Ala Thr Phe Tyr Ala Ile Cys
    2150                2155                2160

Gln Gln Asp Ser Cys His Gln Glu Gln Val Cys Glu Val Ile Ala
    2165                2170                2175

Ser Tyr Ala His Leu Cys Arg Thr Asn Gly Val Cys Val Asp Trp
    2180                2185                2190

Arg Thr Pro Asp Phe Cys Ala Met Ser Cys Pro Pro Ser Leu Val
    2195                2200                2205

Tyr Asn His Cys Glu His Gly Cys Pro Arg His Cys Asp Gly Asn
    2210                2215                2220

Val Ser Ser Cys Gly Asp His Pro Ser Glu Gly Cys Phe Cys Pro
    2225                2230                2235

Pro Asp Lys Val Met Leu Glu Gly Ser Cys Val Pro Glu Glu Ala
    2240                2245                2250

Cys Thr Gln Cys Ile Gly Glu Asp Gly Val Gln His Gln Phe Leu
    2255                2260                2265

Glu Ala Trp Val Pro Asp His Gln Pro Cys Gln Ile Cys Thr Cys
    2270                2275                2280

Leu Ser Gly Arg Lys Val Asn Cys Thr Thr Gln Pro Cys Pro Thr
    2285                2290                2295

Ala Lys Ala Pro Thr Cys Gly Leu Cys Glu Val Ala Arg Leu Arg
    2300                2305                2310

Gln Asn Ala Asp Gln Cys Cys Pro Glu Tyr Glu Cys Val Cys Asp
    2315                2320                2325

Pro Val Ser Cys Asp Leu Pro Pro Val Pro His Cys Glu Arg Gly
    2330                2335                2340
```

-continued

```
Leu Gln Pro Thr Leu Thr Asn Pro Gly Glu Cys Arg Pro Asn Phe
2345                2350                2355

Thr Cys Ala Cys Arg Lys Glu Glu Cys Lys Arg Val Ser Pro Pro
2360                2365                2370

Ser Cys Pro Pro His Arg Leu Pro Thr Leu Arg Lys Thr Gln Cys
2375                2380                2385

Cys Asp Glu Tyr Glu Cys Ala Cys Asn Cys Val Asn Ser Thr Val
2390                2395                2400

Ser Cys Pro Leu Gly Tyr Leu Ala Ser Thr Ala Thr Asn Asp Cys
2405                2410                2415

Gly Cys Thr Thr Thr Thr Cys Leu Pro Asp Lys Val Cys Val His
2420                2425                2430

Arg Ser Thr Ile Tyr Pro Val Gly Gln Phe Trp Glu Glu Gly Cys
2435                2440                2445

Asp Val Cys Thr Cys Thr Asp Met Glu Asp Ala Val Met Gly Leu
2450                2455                2460

Arg Val Ala Gln Cys Ser Gln Lys Pro Cys Glu Asp Ser Cys Arg
2465                2470                2475

Ser Gly Phe Thr Tyr Val Leu His Glu Gly Glu Cys Cys Gly Arg
2480                2485                2490

Cys Leu Pro Ser Ala Cys Glu Val Val Thr Gly Ser Pro Arg Gly
2495                2500                2505

Asp Ser Gln Ser Ser Trp Lys Ser Val Gly Ser Gln Trp Ala Ser
2510                2515                2520

Pro Glu Asn Pro Cys Leu Ile Asn Glu Cys Val Arg Val Lys Glu
2525                2530                2535

Glu Val Phe Ile Gln Gln Arg Asn Val Ser Cys Pro Gln Leu Glu
2540                2545                2550

Val Pro Val Cys Pro Ser Gly Phe Gln Leu Ser Cys Lys Thr Ser
2555                2560                2565

Ala Cys Cys Pro Ser Cys Arg Cys Glu Arg Met Glu Ala Cys Met
2570                2575                2580

Leu Asn Gly Thr Val Ile Gly Pro Gly Lys Thr Val Met Ile Asp
2585                2590                2595

Val Cys Thr Thr Cys Arg Cys Met Val Gln Val Gly Val Ile Ser
2600                2605                2610

Gly Phe Lys Leu Glu Cys Arg Lys Thr Thr Cys Asn Pro Cys Pro
2615                2620                2625

Leu Gly Tyr Lys Glu Glu Asn Asn Thr Gly Glu Cys Cys Gly Arg
2630                2635                2640

Cys Leu Pro Thr Ala Cys Thr Ile Gln Leu Arg Gly Gly Gln Ile
2645                2650                2655

Met Thr Leu Lys Arg Asp Glu Thr Leu Gln Asp Gly Cys Asp Thr
2660                2665                2670

His Phe Cys Lys Val Asn Glu Arg Gly Glu Tyr Phe Trp Glu Lys
2675                2680                2685

Arg Val Thr Gly Cys Pro Pro Phe Asp Glu His Lys Cys Leu Ala
2690                2695                2700

Glu Gly Gly Lys Ile Met Lys Ile Pro Gly Thr Cys Cys Asp Thr
2705                2710                2715

Cys Glu Glu Pro Glu Cys Asn Asp Ile Thr Ala Arg Leu Gln Tyr
2720                2725                2730

Val Lys Val Gly Ser Cys Lys Ser Glu Val Glu Val Asp Ile His
```

```
                    2735                  2740                  2745
Tyr Cys Gln Gly Lys Cys Ala Ser Lys Ala Met Tyr Ser Ile Asp
        2750                  2755                  2760

Ile Asn Asp Val Gln Asp Gln Cys Ser Cys Ser Pro Thr Arg
    2765                  2770                  2775

Thr Glu Pro Met Gln Val Ala Leu His Cys Thr Asn Gly Ser Val
2780                  2785                  2790

Val Tyr His Glu Val Leu Asn Ala Met Glu Cys Lys Cys Ser Pro
    2795                  2800                  2805

Arg Lys Cys Ser Lys
    2810

<210> SEQ ID NO 2
<211> LENGTH: 1365
<212> TYPE: PRT
<213> ORGANISM: Homo sapiens

<400> SEQUENCE: 2

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
50                  55                  60

Pro Cys Phe His Gln Lys Glu Tyr Ala Pro Gly Glu Thr Val Lys
65                  70                  75                  80

Ile Gly Cys Asn Thr Cys Val Cys Gln Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285
```

```
Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
        435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly Leu
465                 470                 475                 480

Val Val Pro Pro Thr Asp Ala Pro Val Ser Pro Thr Thr Leu Tyr Val
                485                 490                 495

Glu Asp Ile Ser Glu Pro Pro Leu His Asp Phe Tyr Cys Ser Arg Leu
            500                 505                 510

Leu Asp Leu Val Phe Leu Leu Asp Gly Ser Ser Arg Leu Ser Glu Ala
        515                 520                 525

Glu Phe Glu Val Leu Lys Ala Phe Val Val Asp Met Met Glu Arg Leu
530                 535                 540

Arg Ile Ser Gln Lys Trp Val Arg Val Ala Val Val Glu Tyr His Asp
545                 550                 555                 560

Gly Ser His Ala Tyr Ile Gly Leu Lys Asp Arg Lys Arg Pro Ser Glu
                565                 570                 575

Leu Arg Arg Ile Ala Ser Gln Val Lys Tyr Ala Gly Ser Gln Val Ala
            580                 585                 590

Ser Thr Ser Glu Val Leu Lys Tyr Thr Leu Phe Gln Ile Phe Ser Lys
        595                 600                 605

Ile Asp Arg Pro Glu Ala Ser Arg Ile Thr Leu Leu Leu Met Ala Ser
610                 615                 620

Gln Glu Pro Gln Arg Met Ser Arg Asn Phe Val Arg Tyr Val Gln Gly
625                 630                 635                 640

Leu Lys Lys Lys Lys Val Ile Val Ile Pro Val Gly Ile Gly Pro His
                645                 650                 655

Ala Asn Leu Lys Gln Ile Arg Leu Ile Glu Lys Gln Ala Pro Glu Asn
            660                 665                 670

Lys Ala Phe Val Leu Ser Ser Val Asp Glu Leu Glu Gln Gln Arg Asp
        675                 680                 685

Glu Ile Val Ser Tyr Leu Cys Asp Leu Ala Pro Glu Ala Pro Pro Pro
690                 695                 700

Thr Leu Pro Pro Asp Met Ala Gln Val Thr Val Gly Pro Gly Leu Leu
```

-continued

```
            705                 710                 715                 720
        Gly Val Ser Thr Leu Gly Pro Lys Arg Asn Ser Met Val Leu Asp Val
                        725                 730                 735
        Ala Phe Val Leu Glu Gly Ser Asp Lys Ile Gly Glu Ala Asp Phe Asn
                        740                 745                 750
        Arg Ser Lys Glu Phe Met Glu Val Ile Gln Arg Met Asp Val Gly
                        755                 760                 765
        Gln Asp Ser Ile His Val Thr Val Leu Gln Tyr Ser Tyr Met Val Thr
            770                 775                 780
        Val Glu Tyr Pro Phe Ser Glu Ala Gln Ser Lys Gly Asp Ile Leu Gln
        785                 790                 795                 800
        Arg Val Arg Glu Ile Arg Tyr Gln Gly Gly Asn Arg Thr Asn Thr Gly
                        805                 810                 815
        Leu Ala Leu Arg Tyr Leu Ser Asp His Ser Phe Leu Val Ser Gln Gly
                        820                 825                 830
        Asp Arg Glu Gln Ala Pro Asn Leu Val Tyr Met Val Thr Gly Asn Pro
                        835                 840                 845
        Ala Ser Asp Glu Ile Lys Arg Leu Pro Gly Asp Ile Gln Val Val Pro
        850                 855                 860
        Ile Gly Val Gly Pro Asn Ala Asn Val Gln Glu Leu Glu Arg Ile Gly
        865                 870                 875                 880
        Trp Pro Asn Ala Pro Ile Leu Ile Gln Asp Phe Glu Thr Leu Pro Arg
                        885                 890                 895
        Glu Ala Pro Asp Leu Val Leu Gln Arg Cys Cys Ser Gly Glu Gly Leu
                        900                 905                 910
        Gln Ile Pro Thr Leu Ser Pro Ala Pro Asp Cys Ser Gln Pro Leu Asp
                        915                 920                 925
        Val Ile Leu Leu Leu Asp Gly Ser Ser Ser Phe Pro Ala Ser Tyr Phe
                        930                 935                 940
        Asp Glu Met Lys Ser Phe Ala Lys Ala Phe Ile Ser Lys Ala Asn Ile
        945                 950                 955                 960
        Gly Pro Arg Leu Thr Gln Val Ser Val Leu Gln Tyr Gly Ser Ile Thr
                        965                 970                 975
        Thr Ile Asp Val Pro Trp Asn Val Val Pro Glu Lys Ala His Leu Leu
                        980                 985                 990
        Ser Leu Val Asp Val Met Gln Arg Glu Gly Gly Pro Ser Gln Ile Gly
                        995                 1000                1005
        Asp Ala Leu Gly Phe Ala Val Arg Tyr Leu Thr Ser Glu Met His
            1010                1015                1020
        Gly Ala Arg Pro Gly Ala Ser Lys Ala Val Val Ile Leu Val Thr
            1025                1030                1035
        Asp Val Ser Val Asp Ser Val Asp Ala Ala Ala Asp Ala Ala Arg
            1040                1045                1050
        Ser Asn Arg Val Thr Val Phe Pro Ile Gly Ile Gly Asp Arg Tyr
            1055                1060                1065
        Asp Ala Ala Gln Leu Arg Ile Leu Ala Gly Pro Ala Gly Asp Ser
            1070                1075                1080
        Asn Val Val Lys Leu Gln Arg Ile Glu Asp Leu Pro Thr Met Val
            1085                1090                1095
        Thr Leu Gly Asn Ser Phe Leu His Lys Leu Cys Ser Gly Phe Val
            1100                1105                1110
        Arg Ile Cys Met Asp Glu Asp Gly Asn Glu Lys Arg Pro Gly Asp
            1115                1120                1125
```

```
Val Trp Thr Leu Pro Asp Gln Cys His Thr Val Thr Cys Gln Pro
    1130                1135                1140

Asp Gly Gln Thr Leu Leu Lys Ser His Arg Val Asn Cys Asp Arg
    1145                1150                1155

Gly Leu Arg Pro Ser Cys Pro Asn Ser Gln Ser Pro Val Lys Val
    1160                1165                1170

Glu Glu Thr Cys Gly Cys Arg Trp Thr Cys Pro Cys Val Cys Thr
    1175                1180                1185

Gly Ser Ser Thr Arg His Ile Val Thr Phe Asp Gly Gln Asn Phe
    1190                1195                1200

Lys Leu Thr Gly Ser Cys Ser Tyr Val Leu Phe Gln Asn Lys Glu
    1205                1210                1215

Gln Asp Leu Glu Val Ile Leu His Asn Gly Ala Cys Ser Pro Gly
    1220                1225                1230

Ala Arg Gln Gly Cys Met Lys Ser Ile Glu Val Lys His Ser Ala
    1235                1240                1245

Leu Ser Val Glu Leu His Ser Asp Met Glu Val Thr Val Asn Gly
    1250                1255                1260

Arg Leu Val Ser Val Pro Tyr Val Gly Gly Asn Met Glu Val Asn
    1265                1270                1275

Val Tyr Gly Ala Ile Met His Glu Val Arg Phe Asn His Leu Gly
    1280                1285                1290

His Ile Phe Thr Phe Thr Pro Gln Asn Asn Glu Phe Gln Leu Gln
    1295                1300                1305

Leu Ser Pro Lys Thr Phe Ala Ser Lys Thr Tyr Gly Leu Cys Gly
    1310                1315                1320

Ile Cys Asp Glu Asn Gly Ala Asn Asp Phe Met Leu Arg Asp Gly
    1325                1330                1335

Thr Val Thr Thr Asp Trp Lys Thr Leu Val Gln Glu Trp Thr Val
    1340                1345                1350

Gln Arg Pro Gly Gln Thr Cys Gln Pro Ile Leu Glu
    1355                1360                1365

<210> SEQ ID NO 3
<211> LENGTH: 272
<212> TYPE: PRT
<213> ORGANISM: Homo sapiens

<400> SEQUENCE: 3

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Gln Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
```

```
            115                 120                 125
Val Leu Val Gln Asp Tyr Cys Gly Ser Asn Pro Gly Thr Phe Arg Ile
            130                 135                 140
Leu Val Gly Asn Lys Gly Cys Ser His Pro Ser Val Lys Cys Lys Lys
145                 150                 155                 160
Arg Val Thr Ile Leu Val Glu Gly Gly Glu Ile Glu Leu Phe Asp Gly
                    165                 170                 175
Glu Val Asn Val Lys Arg Pro Met Lys Asp Glu Thr His Phe Glu Val
            180                 185                 190
Val Glu Ser Gly Arg Tyr Ile Ile Leu Leu Gly Lys Ala Leu Ser
            195                 200                 205
Val Val Trp Asp Arg His Leu Ser Ile Ser Val Val Leu Lys Gln Thr
            210                 215                 220
Tyr Gln Glu Lys Val Cys Gly Leu Cys Gly Asn Phe Asp Gly Ile Gln
225                 230                 235                 240
Asn Asn Asp Leu Thr Ser Ser Asn Leu Gln Val Glu Glu Asp Pro Val
                    245                 250                 255
Asp Phe Gly Asn Ser Trp Lys Val Ser Ser Gln Cys Ala Asp Thr Arg
            260                 265                 270

<210> SEQ ID NO 4
<211> LENGTH: 910
<212> TYPE: PRT
<213> ORGANISM: Homo sapiens

<400> SEQUENCE: 4

Ser Leu Ser Cys Arg Pro Pro Met Val Lys Leu Val Cys Pro Ala Asp
1               5                   10                  15
Asn Leu Arg Ala Glu Gly Leu Glu Cys Thr Lys Thr Cys Gln Asn Tyr
            20                  25                  30
Asp Leu Glu Cys Met Ser Met Gly Cys Val Ser Gly Cys Leu Cys Pro
        35                  40                  45
Pro Gly Met Val Arg His Glu Asn Arg Cys Val Ala Leu Glu Arg Cys
50                  55                  60
Pro Cys Phe His Gln Gly Lys Glu Tyr Ala Pro Gly Glu Thr Val Lys
65                  70                  75                  80
Ile Gly Cys Asn Thr Cys Val Cys Gln Asp Arg Lys Trp Asn Cys Thr
                85                  90                  95
Asp His Val Cys Asp Ala Thr Cys Ser Thr Ile Gly Met Ala His Tyr
            100                 105                 110
Leu Thr Phe Asp Gly Leu Lys Tyr Leu Phe Pro Gly Glu Cys Gln Tyr
        115                 120                 125
Val Leu Val Gln Asp Tyr Cys Gly Ser Asn Pro Gly Thr Phe Arg Ile
            130                 135                 140
Leu Val Gly Asn Lys Gly Cys Ser His Pro Ser Val Lys Cys Lys Lys
145                 150                 155                 160
Arg Val Thr Ile Leu Val Glu Gly Gly Glu Ile Glu Leu Phe Asp Gly
                    165                 170                 175
Glu Val Asn Val Lys Arg Pro Met Lys Asp Glu Thr His Phe Glu Val
            180                 185                 190
Val Glu Ser Gly Arg Tyr Ile Ile Leu Leu Gly Lys Ala Leu Ser
            195                 200                 205
Val Val Trp Asp Arg His Leu Ser Ile Ser Val Val Leu Lys Gln Thr
            210                 215                 220
```

```
Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
            245                 250                 255

Asp Phe Gly Asn Ser Trp Lys Val Ser Ser Gln Cys Ala Asp Thr Arg
                260                 265                 270

Lys Val Pro Leu Asp Ser Ser Pro Ala Thr Cys His Asn Asn Ile Met
            275                 280                 285

Lys Gln Thr Met Val Asp Ser Ser Cys Arg Ile Leu Thr Ser Asp Val
290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
                340                 345                 350

Lys Val Val Thr Trp Arg Thr Ala Thr Leu Cys Pro Gln Ser Cys Glu
            355                 360                 365

Glu Arg Asn Leu Arg Glu Asn Gly Tyr Glu Cys Glu Trp Arg Tyr Asn
370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
                420                 425                 430

Cys Pro Val Cys Glu Val Ala Gly Arg Arg Phe Ala Ser Gly Lys Lys
            435                 440                 445

Val Thr Leu Asn Pro Ser Asp Pro Glu His Cys Gln Ile Cys His Cys
            450                 455                 460

Asp Val Val Asn Leu Thr Cys Glu Ala Cys Gln Glu Pro Gly Gly Leu
465                 470                 475                 480

Val Val Pro Pro Thr Asp Ala Pro Val Ser Pro Thr Thr Leu Tyr Val
                485                 490                 495

Glu Asp Ile Ser Glu Pro Pro Leu His Asp Phe Tyr Cys Ser Arg Leu
                500                 505                 510

Leu Asp Leu Val Phe Leu Leu Asp Gly Ser Ser Arg Leu Ser Glu Ala
            515                 520                 525

Glu Phe Glu Val Leu Lys Ala Phe Val Val Asp Met Met Glu Arg Leu
530                 535                 540

Arg Ile Ser Gln Lys Trp Val Arg Val Ala Val Val Glu Tyr His Asp
545                 550                 555                 560

Gly Ser His Ala Tyr Ile Gly Leu Lys Asp Arg Lys Arg Pro Ser Glu
                565                 570                 575

Leu Arg Arg Ile Ala Ser Gln Val Lys Tyr Ala Gly Ser Gln Val Ala
                580                 585                 590

Ser Thr Ser Glu Val Leu Lys Tyr Thr Leu Phe Gln Ile Phe Ser Lys
            595                 600                 605

Ile Asp Arg Pro Glu Ala Ser Arg Ile Thr Leu Leu Leu Met Ala Ser
            610                 615                 620

Gln Glu Pro Gln Arg Met Ser Arg Asn Phe Val Arg Tyr Val Gln Gly
625                 630                 635                 640

Leu Lys Lys Lys Lys Val Ile Val Ile Pro Val Gly Ile Gly Pro His
```

```
            645                 650                 655
Ala Asn Leu Lys Gln Ile Arg Leu Ile Glu Lys Gln Ala Pro Glu Asn
            660                 665                 670

Lys Ala Phe Val Leu Ser Ser Val Asp Glu Leu Glu Gln Gln Arg Asp
            675                 680                 685

Glu Ile Val Ser Tyr Leu Cys Asp Leu Ala Pro Glu Ala Pro Pro Pro
        690                 695                 700

Thr Leu Pro Pro Asp Met Ala Gln Val Thr Val Gly Pro Gly Leu Leu
705                 710                 715                 720

Gly Val Ser Thr Leu Gly Pro Lys Arg Asn Ser Met Val Leu Asp Val
                725                 730                 735

Ala Phe Val Leu Glu Gly Ser Asp Lys Ile Gly Glu Ala Asp Phe Asn
                740                 745                 750

Arg Ser Lys Glu Phe Met Glu Glu Val Ile Gln Arg Met Asp Val Gly
            755                 760                 765

Gln Asp Ser Ile His Val Thr Val Leu Gln Tyr Ser Tyr Met Val Thr
        770                 775                 780

Val Glu Tyr Pro Phe Ser Glu Ala Gln Ser Lys Gly Asp Ile Leu Gln
785                 790                 795                 800

Arg Val Arg Glu Ile Arg Tyr Gln Gly Gly Asn Arg Thr Asn Thr Gly
                805                 810                 815

Leu Ala Leu Arg Tyr Leu Ser Asp His Ser Phe Leu Val Ser Gln Gly
                820                 825                 830

Asp Arg Glu Gln Ala Pro Asn Leu Val Tyr Met Val Thr Gly Asn Pro
            835                 840                 845

Ala Ser Asp Glu Ile Lys Arg Leu Pro Gly Asp Ile Gln Val Val Pro
        850                 855                 860

Ile Gly Val Gly Pro Asn Ala Asn Val Gln Glu Leu Glu Arg Ile Gly
865                 870                 875                 880

Trp Pro Asn Ala Pro Ile Leu Ile Gln Asp Phe Glu Thr Leu Pro Arg
                885                 890                 895

Glu Ala Pro Asp Leu Val Leu Gln Arg Cys Cys Ser Gly Glu
            900                 905                 910

<210> SEQ ID NO 5
<211> LENGTH: 272
<212> TYPE: PRT
<213> ORGANISM: Homo sapiens

<400> SEQUENCE: 5

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65              70                  75                  80

Ile Gly Cys Asn Thr Cys Val Cys Gln Asp Arg Lys Trp Asn Cys Thr
                85                  90                  95

Asp His Val Cys Asp Ala Thr Cys Ser Thr Ile Gly Met Ala His Tyr
            100                 105                 110
```

Leu Thr Phe Asp Gly Leu Lys Tyr Leu Phe Pro Gly Glu Cys Gln Tyr
            115                 120                 125

Val Leu Val Gln Asp Tyr Cys Gly Ser Asn Pro Gly Thr Phe Arg Ile
        130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Thr His Phe Glu Val
            180                 185                 190

Val Glu Ser Gly Arg Tyr Ile Ile Leu Leu Gly Lys Ala Leu Ser
            195                 200                 205

Val Val Trp Asp Arg His Leu Ser Ile Ser Val Val Leu Lys Gln Thr
        210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

<210> SEQ ID NO 6
<211> LENGTH: 174
<212> TYPE: PRT
<213> ORGANISM: Homo sapiens

<400> SEQUENCE: 6

Val Ile Leu Leu Leu Asp Gly Ser Ser Ser Phe Pro Ala Ser Tyr Phe
1               5                   10                  15

Asp Glu Met Lys Ser Phe Ala Lys Ala Phe Ile Ser Lys Ala Asn Ile
            20                  25                  30

Gly Pro Arg Leu Thr Gln Val Ser Val Leu Gln Tyr Gly Ser Ile Thr
        35                  40                  45

Thr Ile Asp Val Pro Trp Asn Val Val Pro Glu Lys Ala His Leu Leu
    50                  55                  60

Ser Leu Val Asp Val Met Gln Arg Glu Gly Gly Pro Ser Gln Ile Gly
65                  70                  75                  80

Asp Ala Leu Gly Phe Ala Val Arg Tyr Leu Thr Ser Glu Met His Gly
                85                  90                  95

Ala Arg Pro Gly Ala Ser Lys Ala Val Val Ile Leu Val Thr Asp Val
            100                 105                 110

Ser Val Asp Ser Val Asp Ala Ala Ala Asp Ala Ala Arg Ser Asn Arg
        115                 120                 125

Val Thr Val Phe Pro Ile Gly Ile Gly Asp Arg Tyr Asp Ala Ala Gln
    130                 135                 140

Leu Arg Ile Leu Ala Gly Pro Ala Gly Asp Ser Asn Val Val Lys Leu
145                 150                 155                 160

Gln Arg Ile Glu Asp Leu Pro Thr Met Val Thr Leu Gly Asn
                165                 170

<210> SEQ ID NO 7
<211> LENGTH: 390
<212> TYPE: PRT
<213> ORGANISM: Homo sapiens

<400> SEQUENCE: 7

-continued

```
Gln Cys Ile Gly Glu Asp Gly Val Gln His Gln Phe Leu Glu Ala Trp
1               5                   10                  15

Val Pro Asp His Gln Pro Cys Gln Ile Cys Thr Cys Leu Ser Gly Arg
            20                  25                  30

Lys Val Asn Cys Thr Thr Gln Pro Cys Pro Thr Ala Lys Ala Pro Thr
                35                  40                  45

Cys Gly Leu Cys Glu Val Ala Arg Leu Arg Gln Asn Ala Asp Gln Cys
50                  55                  60

Cys Pro Glu Tyr Glu Cys Val Cys Asp Pro Val Ser Cys Asp Leu Pro
65                  70                  75                  80

Pro Val Pro His Cys Glu Arg Gly Leu Gln Pro Thr Leu Thr Asn Pro
            85                  90                  95

Gly Glu Cys Arg Pro Asn Phe Thr Cys Ala Cys Arg Lys Glu Glu Cys
                100                 105                 110

Lys Arg Val Ser Pro Pro Ser Cys Pro Pro His Arg Leu Pro Thr Leu
            115                 120                 125

Arg Lys Thr Gln Cys Cys Asp Glu Tyr Glu Cys Ala Cys Asn Cys Val
130                 135                 140

Asn Ser Thr Val Ser Cys Pro Leu Gly Tyr Leu Ala Ser Thr Ala Thr
145                 150                 155                 160

Asn Asp Cys Gly Cys Thr Thr Thr Thr Cys Leu Pro Asp Lys Val Cys
                165                 170                 175

Val His Arg Ser Thr Ile Tyr Pro Val Gly Gln Phe Trp Glu Glu Gly
            180                 185                 190

Cys Asp Val Cys Thr Cys Thr Asp Met Glu Asp Ala Val Met Gly Leu
                195                 200                 205

Arg Val Ala Gln Cys Ser Gln Lys Pro Cys Glu Asp Ser Cys Arg Ser
210                 215                 220

Gly Phe Thr Tyr Val Leu His Glu Gly Glu Cys Cys Gly Arg Cys Leu
225                 230                 235                 240

Pro Ser Ala Cys Glu Val Val Thr Gly Ser Pro Arg Gly Asp Ser Gln
                245                 250                 255

Ser Ser Trp Lys Ser Val Gly Ser Gln Trp Ala Ser Pro Glu Asn Pro
            260                 265                 270

Cys Leu Ile Asn Glu Cys Val Arg Val Lys Glu Val Phe Ile Gln
                275                 280                 285

Gln Arg Asn Val Ser Cys Pro Gln Leu Glu Val Pro Val Cys Pro Ser
290                 295                 300

Gly Phe Gln Leu Ser Cys Lys Thr Ser Ala Cys Cys Pro Ser Cys Arg
305                 310                 315                 320

Cys Glu Arg Met Glu Ala Cys Met Leu Asn Gly Thr Val Ile Gly Pro
                325                 330                 335

Gly Lys Thr Val Met Ile Asp Val Cys Thr Thr Cys Arg Cys Met Val
            340                 345                 350

Gln Val Gly Val Ile Ser Gly Phe Lys Leu Glu Cys Arg Lys Thr Thr
            355                 360                 365

Cys Asn Pro Cys Pro Leu Gly Tyr Lys Glu Glu Asn Asn Thr Gly Glu
    370                 375                 380

Cys Cys Gly Arg Cys Leu
385                 390
```